United States Patent
Horn et al.

(10) Patent No.: US 9,089,562 B2
(45) Date of Patent: Jul. 28, 2015

(54) COMPOSITIONS AND METHODS FOR THE TREATMENT OF PRESBYOPIA

(71) Applicant: Presbyopia Therapies, LLC, Coronado, CA (US)

(72) Inventors: Gerald Horn, Deerfield, IL (US); Lee Nordan, Dana Point, CA (US)

(73) Assignee: Presbyopia Therapies LLC, Coronado, CA (US)

( * ) Notice: Subject to any disclaimer, the term of this patent is extended or adjusted under 35 U.S.C. 154(b) by 0 days.

(21) Appl. No.: 14/223,639

(22) Filed: Mar. 24, 2014

(65) Prior Publication Data

US 2015/0065511 A1    Mar. 5, 2015

Related U.S. Application Data

(60) Provisional application No. 61/938,438, filed on Feb. 11, 2014, provisional application No. 61/917,620, filed on Dec. 18, 2013, provisional application No. 61/904,510, filed on Nov. 15, 2013, provisional application No. 61/882,998, filed on Sep. 26, 2013, provisional application No. 61/871,215, filed on Aug. 28, 2013.

(51) Int. Cl.
| | | |
|---|---|---|
| A61K 31/00 | (2006.01) | |
| A61K 31/439 | (2006.01) | |
| A61K 31/4409 | (2006.01) | |
| A61K 31/498 | (2006.01) | |
| A61K 45/06 | (2006.01) | |
| A61K 9/00 | (2006.01) | |
| A61K 31/165 | (2006.01) | |
| A61K 31/4164 | (2006.01) | |

(52) U.S. Cl.
CPC ............ *A61K 31/439* (2013.01); *A61K 9/00* (2013.01); *A61K 31/165* (2013.01); *A61K 31/4164* (2013.01); *A61K 31/4409* (2013.01); *A61K 31/498* (2013.01); *A61K 45/06* (2013.01)

(58) Field of Classification Search
None
See application file for complete search history.

(56) References Cited

U.S. PATENT DOCUMENTS

| | | |
|---|---|---|
| 6,291,466 B1 | 9/2001 | Gwon et al. |
| 6,410,544 B1 | 6/2002 | Gwon et al. |
| 8,299,079 B2 | 10/2012 | Kaufman |
| 8,455,494 B2 | 6/2013 | Kaufman |
| 8,501,800 B2 | 8/2013 | Bowman et al. |
| 2006/0177430 A1 | 8/2006 | Bhushan et al. |
| 2009/0074786 A1* | 3/2009 | Dor et al. ................... 424/141.1 |
| 2010/0016395 A1 | 1/2010 | Benozzi |
| 2011/0251285 A1* | 10/2011 | Tien et al. ................... 514/635 |
| 2012/0094962 A1 | 4/2012 | Skulachev |
| 2012/0165295 A1* | 6/2012 | Painter et al. ................... 514/86 |
| 2013/0245030 A1 | 9/2013 | Kaufman |

FOREIGN PATENT DOCUMENTS

| | | |
|---|---|---|
| WO | 02/100437 A2 | 12/2002 |
| WO | 2009/077736 A2 | 6/2009 |
| WO | 2010/135731 A1 | 12/2010 |
| WO | 2013/041967 A2 | 3/2013 |

OTHER PUBLICATIONS

Grunberger, J., et al., The pupillary response test as a method to differentiate various types of dementia, Neuropsychiatr, 2009, 23(1), 52-57.
Ward, J.S., et al., 1,2,5-Thiadiazole analogues of aceclidine as potent m1 muscarinic agonists, J Med Chem, Jan. 29, 1988, 41(3), 379-392.
Berge, S. M., et al., "Pharmaceutical Salts", Journal of Pharmaceutical Science, 1977, 66, 1-19.
AKORN Incorporated MSDS:Tropicacyl (R); Rev. 11-11.
Mayo Clinic: Tropicamide (Opthalmic Route), 2015, http://www.mayoclinic.org/drugs-supplements/tropicamide-ophthalmic-route/description/drg-20066481.
Chung, S.T. et al., The effect of dioptric blur on reading performance, Vision Res, Jun. 2007, 47(12), 1584-94.
Cowan, E.C. et al., Clinical evaluation of a new mydriatic-mydrilate, Br J Ophthalmol, Dec. 1962, 46(12), 730-6.
Davidson, S., General medicine and visual side effects, Br Med J, Mar. 24, 1979, 1(6166), 821.
Drance, S.M., Dose response of human intraocular pressure to aceclidine, Arch Ophthalmol, Oct. 1972, 88(4), 394-6.
Edwards, R.S., Behaviour of the fellow eye in acute angle-closure glaucoma, Br J Ophthalmol, Sep. 1982, 66(9), 576-9.
Gardiner, P.A., ABC of Ophthalmology: Methods of examination, Br Med J, Dec. 9, 1978, 2(6152),1622-6.
Gardiner, P.A., ABC of Ophthalmology: accidents and first aid, Br Med J, Nov. 11, 1978, 2(6148),1347-50.
Hoyng, F.J., The combination of guanethidine 3% and adrenaline 0.5% in 1 eyedrop (GA) in glaucoma treatment, Br J Ophthalmol, Jan. 1979, 63(1), 56-62.
Mohan, K., Optimal dosage of cyclopentolate 1% for cycloplegic refraction in hypermetropes with brown irides, Indian J Ophthalmol, Nov.-Dec. 2011, 59(6), 514-6.
Nayak, B.K., A comparison of cycloplegic and manifest refractions on the NR-1000F (an objective Auto Refractometer), Br J Ophthalmol, Jan. 1987, 71(1), 73-5.
Park, J.H., The comparison of mydriatic effect between two drugs of different mechanism, Korean J Ophthalmol, Mar. 2009, 23(1), 40-2.
Romano, J.H., Double-blind cross-over comparison of aceclidine and pilocarpine in open-angle glaucoma, Br J Ophthalmol, Aug. 1970, 54(8), 510-21.

(Continued)

*Primary Examiner* — David J Blanchard
*Assistant Examiner* — Sarah Chickos
(74) *Attorney, Agent, or Firm* — Wood Phillips, Katz, Clark & Mortimer

(57) ABSTRACT

The invention provides compositions and methods for the treatment of presbyopia. The compositions preferably use aceclidine separate or together with a cycloplegic agent and/or with a nonionic surfactant and viscosity enhancer, and or with low concentrations of a selective α-2 adrenergic receptor agonist.

15 Claims, 1 Drawing Sheet

(56) References Cited

OTHER PUBLICATIONS

Smith, S.A., Subsensitivity to cholinoceptor stimulation of the human iris sphincter in situ following acute and chronic administration of cholinomimetic miotic drugs, Br J Pharmacol, Jul. 1980, 69(3), 513-8.

Tataru, C.P., Antiglaucoma pharmacotherapy, J Med Life, Sep. 15, 2012, 5(3), 247-51.

Trinavarat, A., Effective pupil dilatation with a mixture of 0.75% tropicamide and 2.5% phenylephrine: A randomized controlled trial, Indian J Ophthalmol, Sep.-Oct. 2009, 57(5), 351-4.

Wood, J.M., Pupil dilatation does affect some aspects of daytime driving performance, Br J Ophthalmol, Nov. 2003, 87 (11), 1387-90.

International Search Report and Written Opinion for corresponding PCT Application No. PCT/US2014/052256 mailed Dec. 18, 2014.

* cited by examiner

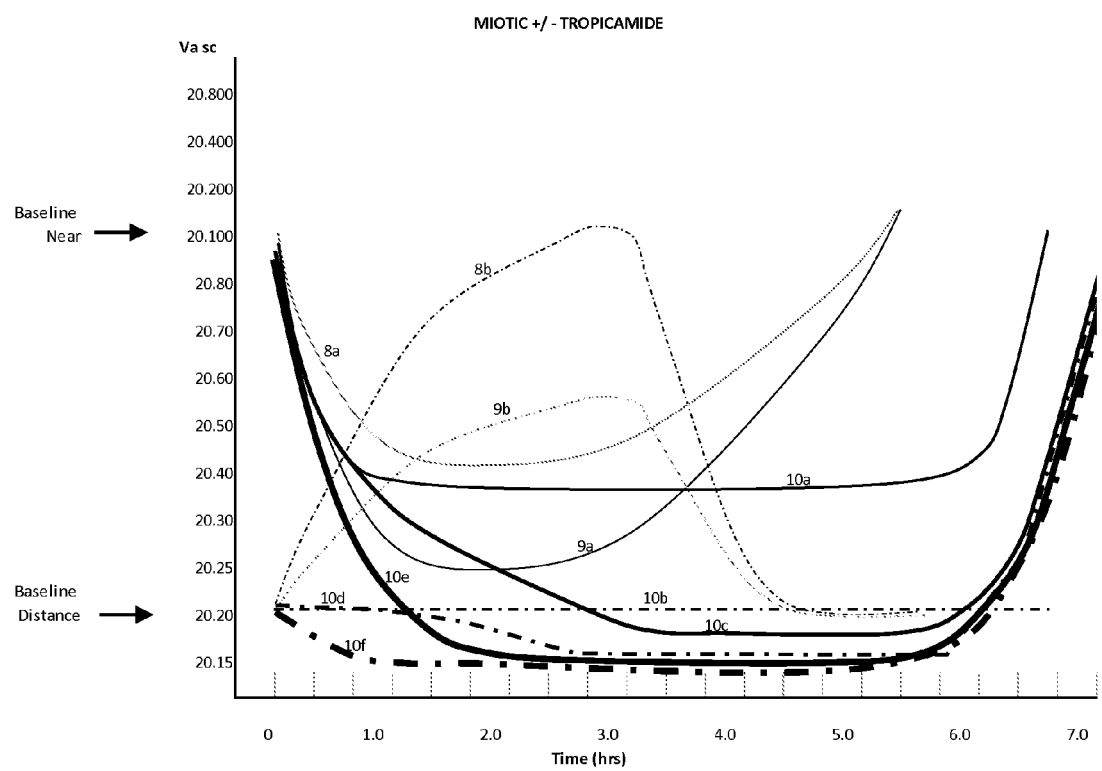

COMPOSITIONS AND METHODS FOR THE TREATMENT OF PRESBYOPIA

BACKGROUND OF THE INVENTION

As a person ages the minimum distance from the eye at which an object will come into focus, provided distance vision is corrected or is excellent unaided, increases. For example, a 10 year-old can focus on an object or a "focal point" only three inches (0.072 meters) from their eye while still retaining excellent distance vision; a 40 year-old at six inches (0.15 meters); and a 60 year-old at an inconvenient 39 inches (1.0 meter). This condition of increasing minimum focal length in individuals with excellent unaided distance vision is called presbyopia, loosely translated as "old-man eye".

Excellent unaided distance vision is also known as emmetropia. The inability to focus on distant focal points is known as myopia and the inability to focus on near focal points is known as hyperopia. Specifically, "distance" vision is considered any focal point 1 meter or more from the eye and near vision is any focal point less than 1 meter from the eye. The minimum focal length at which an object will come into focus is known as the "near point". The change in focus from distance to the near point and any focal point in between is called accommodation. Accommodation is often measured in diopters. Diopters are calculated by taking the reciprocal of the focal length (in meters). For example, the decrease in accommodation from a 10 year-old eye to a 60 year-old eye is about 13 diopters (1÷0.072 meters=13.89 diopters; 1÷1 meter=1 diopter).

The highest incidence of first complaint of presbyopia occurs in people ages 42-44. Presbyopia occurs because as a person ages the eye's accommodative ability which uses near reflex-pupil constriction, convergence of the eyes and particularly ciliary muscle contraction, decreases. This reduction in accommodation results in an inadequate change in the normal thickening and increased curvature of the anterior surface of the lens that is necessary for the shift in focus from distant objects to near objects. Important near focus tasks affected by presbyopia include viewing computer screens (21 inches) and reading print (16 inches).

Presbyopia is a normal and inevitable effect of ageing and is the first unmistakable sign for many in their forties that they are getting older. One study found that more than 1 billion people worldwide were presbyopic in 2005. This same study predicted that number to almost double by the year 2050. If everyone over the age of 45 is considered to be presbyopic, then an estimated 122 million people in the United States alone had presbyopia in 2010. As baby boomers reach the critical age, this number is only going to increase.

Presbyopia carries with it a stigma resulting from the limitation in ability to quickly function at many tasks requiring focusing at both distant and near points, which once occurred almost immediately. In the presbyopic patient, these tasks can be performed only by the use of eyeglasses, contact lenses or after undergoing invasive surgery. One such optical modification, the monovision procedure, can be executed with the use of glasses, contact lenses or even surgery. The monovision procedure corrects one eye for near focus and the other eye for distance focus. However, monovision correction is normally accompanied by loss of depth perception and distance vision particularly in dim light (e.g. night). Other surgical procedures that have been developed to relieve presbyopia include: (1) the implantation of intraocular lenses (INTRACOR®; registered trademark of Technolas Perfect Vision GMBH); (2) reshaping of the cornea (PresbyLASIK and conductive keratoplasty); (3) scleral band expansion; and (4) implantation of corneal inlays (Flexivue Microlens®; registered trademark of PresbiBio LLC, Kamra®; registered trademark of AcuFocus, Inc. and Vue+). Kamra® corneal inlays manufactured by AcuFocus work by inlaying a pinhole on the cornea to increase the depth of focus. A similar effect can be achieved with general miotic agents, such as pilocarpine (a non-selective muscarinic acetylcholine receptor agonist), carbachol (a non-selective muscarinic acetylcholine receptor agonist), and phospholine iodide (an acetylcholinesterase inhibitor). These general miotic agents trigger increased ciliary muscle contraction and induce accommodation of any remaining reserves, improving near vision at the expense of distance vision in individuals who still retain some accommodative function. While these general miotic agents also create improved depth of focus via a pinhole effect induced by pupillary miosis (i.e. constriction), to the degree accommodation occurs, the pinhole effect only partially offsets the induced accommodative myopia for distance. In some cases, such as with pilocarpine or carbachol, the induced accommodation may create up to 5 diopters or more of induced myopia resulting in induced myopia causing blurred distance vision generally and during shift of the focal point from distance to near. These general miotic agents also cause substantial redness, severe nasal congestion and create ciliary muscle spasms, which commonly induces discomfort that can be severe and long-lasting. In extreme cases, such ciliary muscle spasms can result in retinal detachment.

Miotic agents have been described in various patent and patent applications for the treatment of presbyopia. U.S. Pat. Nos. 6,291,466 and 6,410,544 describe the use of pilocarpine to regulate the contraction of ciliary muscles to restore the eye to its resting state and potentially restore its accommodative abilities.

US Patent Application Publication No. 2010/0016395 describes the use of pilocarpine with the non-steroidal anti-inflammatory, diclofenac, to reduce brow ache from ciliary spasm and increase the time in which the ciliary muscle contraction is regulated. International PCT Application Publication WO/2013/041967 describes the use of pilocarpine with oxymetazoline or meloxicam to temporarily overcome ocular conditions such as presbyopia.

U.S. Pat. No. 8,299,079 (HEK Development LLC) describes the use of direct acting general miotic agents such as pilocarpine, carbachol and phospholine iodide with brimonidine at a concentration from 0.05% to 3.0% w/v. However, the use of brimonidine concentrations at or above 0.05% w/v results in increased rebound hyperemia. For example, rebound redness occurs in 25% of patients using brimonidine 0.20% w/v (Alphagan®, registered trademark of Allergan, Inc.) twice daily.

These attempts at miotic treatment for presbyopia all induce transient myopia of several diopters reducing distance vision to about legal blindness or worse at the expense of improved near vision for the full duration of their action, typically lasting several hours.

Thus, there is a need in the art for a treatment of presbyopia that is non-invasive and convenient with minimal side effects. Specifically, there is a need for an ophthalmological composition that will allow a person suffering from presbyopia to focus on near objects without significant side effects such as diminished distance vision, blurred vision, pain, redness, impaired night driving or incapacitating dim light vision, induced nasal congestion, or risk of retinal detachment. Further, such treatment should provide quick onset in minutes and a duration of full effect of several hours during which a pupillary miosis of between about 1.65-2.40 mm and more preferably 1.80 mm-about 2.2 mm is achieved.

SUMMARY OF THE INVENTION

In certain embodiments, the present invention is directed to compositions and methods for the treatment of presbyopia.

In certain embodiments, the present invention is directed to compositions and methods for the treatment of presbyopia comprising a muscarinic agonist, wherein the muscarinic agonist preferentially activates M1 and M3 muscarinic acetylcholine receptors. In still more preferred embodiments the muscarinic agonist is more highly selective for M1 than M3. In most preferred embodiments the muscarinic agonist activates M1 only.

In certain embodiments, the present invention is directed to compositions and methods for the treatment of presbyopia comprising a muscarinic agonist of Formula I:

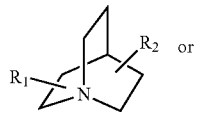

Formula II:

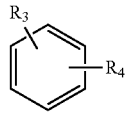

wherein:
$R_1$ is H, O, $CH_3$, an alkyl, acetyl, acyl, an aziridine, nitrile, imine, nitryl-imine methyl substitution, nitryl-imine methyl substitution with ester attached, an aromatic ring, a substituted aromatic ring, an azide, acetamide, a pyridine, a substituted pyridine, a pyrollidine, a substituted pyrollidine, imidazole, a substituted imidazole, an imidazole wherein one or more carbon atoms are replaced by O or S, a substituted imidazole wherein one or more carbon atoms are replaced by O or S, a benzimidazole, a substituted benzimidazole, a benzimidazole wherein one or more carbon atoms are replaced by O or S, or a substituted benzimidazole wherein one or more carbon atoms are replaced by O or S;
$R_2$ is H, O, $CH_3$, an alkyl, acetyl, acyl, nitrile, imine, nitryl-imine methyl substitution, or an ester-O-alkyl;
$R_3$ is H, $CH_3$; acyl, acetyl, or ester; and
$R_4$ is acyl, acetyl, ester, $CH_3$, an alkyl, an aromatic ring, a substituted aromatic ring, cyclohexane, or a substituted cyclohexane ring,
and wherein each of $R_1$ and $R_2$ independently substitute for a H of a —$CH_2$— of the quinuclidine ring.

In certain embodiments, the present invention is directed to compositions and methods for the treatment of presbyopia comprising a muscarinic agonist that preferentially activates M1 and M3 muscarinic acetylcholine receptors.

In certain embodiments, the present invention is directed to compositions and methods for the treatment of presbyopia comprising a muscarinic agonist selected from the group consisting of aceclidine, talsaclidine, sabcomeline, cevimeline, WAY-132983, AFB267B (NGX267), AC-42, AC-260584, 77-LH-28-1, and LY593039 or any pharmaceutically acceptable salts, esters, analogues, prodrugs or derivatives thereof.

In certain embodiments, the present invention is directed to compositions and methods for the treatment of presbyopia comprising a muscarinic agonist that activates only M1 muscarinic acetylcholine receptors.

In certain other embodiments, the present invention is directed to an ophthalmological composition for the treatment of presbyopia comprising aceclidine.

In certain other embodiments the present invention is directed to an ophthalmological composition for the treatment of presbyopia comprising aceclidine and a cycloplegic agent.

In certain other embodiments, the present invention is directed to an ophthalmological composition for the treatment of presbyopia comprising aceclidine and a selective α-2 adrenergic receptor agonist.

In certain other embodiments, the present invention is directed to an ophthalmological composition for the treatment of presbyopia comprising aceclidine, a cycloplegic agent and a selective α-2 adrenergic receptor agonist.

In certain other embodiments, the present invention is directed to an ophthalmological composition for the treatment of presbyopia comprising a general miotic agent and a cycloplegic agent.

In certain other embodiments, the present invention is directed to an ophthalmological composition of the present invention comprising:
a general miotic agent, a compound of Formula I or II, a muscarinic agonist or aceclidine;
optionally a cycloplegic agent;
optionally a selective α-2 adrenergic receptor agonist;
a viscosity enhancer; and
a surfactant selected from the group consisting of an anionic surfactant, a nonionic surfactant, and a combination thereof.

In certain other embodiments, the viscosity enhancer is carboxymethyl cellulose; the anionic surfactant is selected from the group consisting of a gamma cyclodextrin, Captisol® (sulfobutylether(β-cyclodextrin, Captisol is a registered trademark of Cydex Pharmaceuticals), sodium lauryl sulfate and sodium ester lauryl sulfate; and the nonionic surfactant is selected from the group consisting of a poloxamer, a polysorbate, Span® 20-80 (sorbitan monolaurate, sorbitan monopalmitate, sorbitan monostearate, and sorbitan monooleate; Span is a registered trademark of Uniqema Americas Inc.), a polyoxyl alkyl, a cyclodextrin and derivatives thereof.

In certain other embodiments, the present invention is directed to an ophthalmological composition of the present invention comprising:
a general miotic agent, a compound of Formula I or II, a muscarinic agonist or aceclidine;
optionally a cycloplegic agent;
optionally a selective α-2 adrenergic receptor agonist; and
a surfactant selected from the group consisting of Captisol® (sulfobutylether β-cyclodextrin), polyoxyl 40 stearate and 2-hydroxypropyl beta-cyclodextrin.

In certain other embodiments, the present invention is directed to an ophthalmological composition of the present invention comprising:
a general miotic agent, a compound of Formula I or II, a muscarinic agonist or aceclidine;
optionally a cycloplegic agent;
optionally a selective α-2 adrenergic receptor agonist;

a surfactant selected from the group consisting of Captisol® (sulfobutylether β-cyclodextrin), polyoxyl 40 stearate and 2-hydroxypropyl beta-cyclodextrin; and
one or more additional non-ionic surfactants.

In certain other embodiments, the one or more additional non-ionic surfactants is selected from the group consisting of poloxamer 188, polyoxyl 40 stearate, polyoxyl 35 castor oil, polysorbate, Span® 20-80 (sorbitan monolaurate, sorbitan monopalmitate, sorbitan monostearate, and sorbitan monooleate), tyloxapol and combinations thereof.

In certain other embodiments the present invention is directed to an ophthalmological composition of the present invention comprising:
  a general miotic agent, a compound of Formula I or II, a muscarinic agonist or aceclidine;
  optionally a cycloplegic agent; and
  optionally a selective α-2 adrenergic receptor agonist,
  wherein the selective α-2 adrenergic receptor agonist is selected from the group consisting of brimonidine, dexmedetomidine, fadolmidine and guanfacine.

In certain other embodiments, the present invention is directed to an ophthalmological composition of the present invention comprising:
  a general miotic agent, a compound of Formula I or II, a muscarinic agonist or aceclidine;
  optionally a cycloplegic agent; and
  optionally a selective α-2 adrenergic receptor agonist,
  wherein the cycloplegic agent is selected from the group consisting of pirenzepine, tropicamide, Cyclogyl® (cyclopentolate hydrochloride; Cyclogyl is a registered trademark of Alcon Research, LTD), 4-diphenylacetoxy-N-methylpiperidine methiodide (4-DAMP), xanomeline, otenzepad and a combination thereof; in preferred embodiments the cycloplegic agent is tropicamide.

In preferred embodiments, a composition of the present invention has a pH greater than or equal to about 5.5, preferably greater than or equal to 6.0, more preferably greater than or equal to 6.5 and most preferably greater than or equal to 7.0.

In certain other embodiments, the present invention is directed to an ophthalmological composition of the present invention comprising:
  a general miotic agent, a compound of Formula I or II, a muscarinic agonist or aceclidine;
  optionally a cycloplegic agent;
  optionally a selective α-2 adrenergic receptor agonist; and
  an in situ gel.

In preferred embodiments the in situ gel is selected from the group consisting of Carbopol® (polyacrylic acid; Carbopol is a registered trademark of Lubrizol Advanced Materials, Inc.) at a concentration from about 0.0001% to about 0.4% w/v, alginate, pectin, xanthan gum and guar gum.

In preferred embodiments, the present invention is directed to an ophthalmological composition for the treatment of presbyopia comprising:
  aceclidine at a concentration from about 0.25% to about 2.0% w/v;
  tropicamide at a concentration from about 0.025% to about 0.1% w/v;
  carboxymethyl cellulose at a concentration from about 0.1% to about 1.2% w/v; and
  sodium chloride at a concentration from about 0.01% to about 1.0% w/v.

In preferred embodiments, the present invention is directed to an ophthalmological composition for the treatment of presbyopia comprising:
  aceclidine at a concentration from about 0.25% to about 2.0% w/v;
  tropicamide at a concentration from about 0.025% to about 0.1% w/v;
  carboxymethyl cellulose at a concentration from about 0.1% to about 1.2% w/v;
  sodium chloride at a concentration from about 0.01% to about 1.0% w/v; and
  benzalkonium chloride at a concentration from about 0.007% to about 0.01% w/v.

In preferred embodiments, the present invention is directed to an ophthalmological composition for the treatment of presbyopia comprising:
  aceclidine at a concentration from about 0.25% to about 2.0% w/v;
  tropicamide at a concentration from about 0.025% to about 0.1% w/v;
  carboxymethyl cellulose at a concentration from about 0.1% to about 1.2% w/v;
  sodium chloride at a concentration from about 0.01% to about 1.0% w/v; and
  a surfactant at a concentration from about 1% to about 15% w/v.

In preferred embodiments, the present invention is directed to an ophthalmological composition for the treatment of presbyopia comprising:
  aceclidine at a concentration from about 0.25% to about 2.0% w/v;
  tropicamide at a concentration from about 0.025% to about 0.1% w/v;
  carboxymethyl cellulose at a concentration from about 0.1% to about 1.2% w/v;
  sodium chloride at a concentration from about 0.01% to about 1.0% w/v; and
  Captisol® (sulfobutylether β-cyclodextrin) at a concentration from about 5.0% to about 6.0% w/v.

In preferred embodiments, the present invention is directed to an ophthalmological composition for the treatment of presbyopia comprising:
  aceclidine at a concentration from about 0.25% to about 2.0% w/v;
  tropicamide at a concentration from about 0.025% to about 0.1% w/v;
  carboxymethyl cellulose at a concentration from about 0.1% to about 1.2% w/v;
  sodium chloride at a concentration from about 0.01% to about 1.0% w/v; and
  polyoxyl 40 stearate at a concentration from about 5.0% to about 6.0% w/v.

The present invention is further directed to a method for treating presbyopia comprising administering to a patient in need thereof a composition of the present invention.

The present invention is further directed to a method for treating presbyopia comprising administering to a patient in need thereof a composition comprising aceclidine and optionally, an α-2 adrenergic agonist and/or a cycloplegic agent, wherein the treatment can be combined in a single formulation or multiple formulations or by co-administration or a sequential administration of an α-2 adrenergic agonist and/or co-administration or a sequential administration of a cycloplegic agent, or preferably co-administration or sequential administration of both.

The present invention is further directed to a method of increasing the visual depth of field (i.e. depth of focus) comprising administering to a subject in need thereof a pharmaceutically effective amount of an ophthalmological composition of the present invention.

The present invention is further directed to a method of increasing the visual depth perception upon improving near vision unaided comprising administering to a subject in need thereof a pharmaceutically effective amount of an ophthalmological composition of the present invention in both eyes (binocular vision), wherein such binocularity further enhances near vision beyond that of either eye separately.

The present invention is further directed to a method of inducing pupil miosis comprising administering to a subject in need thereof a pharmaceutically effective amount of an ophthalmological composition of the present invention.

The present invention is further directed to a method of inducing pupil miosis comprising administering to a subject in need thereof a pharmaceutically effective amount of an ophthalmological composition of the present invention, wherein the pupil miosis is from about 1.40 to about 2.0 millimeters.

The present invention is further directed to a method of inducing pupil miosis comprising administering to a subject in need thereof a pharmaceutically effective amount of an ophthalmological composition of the present invention, wherein the pupil miosis is from about 1.50 to about 1.70 millimeters.

The present invention is further directed to a method of inducing pupil miosis comprising administering to a subject in need thereof a pharmaceutically effective amount of an ophthalmological composition of the present invention, wherein the pupil miosis is from about 1.80 to about 2.0 millimeters.

The present invention is further directed to a method of inducing pupil miosis comprising administering to a subject in need thereof a pharmaceutically effective amount of an ophthalmological composition of the present invention, wherein the pupil miosis is from about 1.50 to about 1.70 millimeters and wherein the duration of the miotic effect is at least about 4 hours.

The present invention is further directed to a method of inducing pupil miosis comprising administering to a subject in need thereof a pharmaceutically effective amount of an ophthalmological composition of the present invention, wherein the pupil miosis is from about 1.50 to about 1.70 millimeters and wherein the duration of the miotic effect is at least about 6 hours.

The present invention is further directed to a method of inducing pupil miosis comprising administering to a subject in need thereof a pharmaceutically effective amount of an ophthalmological composition of the present invention, wherein the pupil miosis is from about 1.50 to about 1.70 millimeters and wherein the duration of the miotic effect is at least about 7.5 hours.

The present invention is further directed to a method of inducing pupil miosis comprising administering to a subject in need thereof a pharmaceutically effective amount of an ophthalmological composition of the present invention, wherein the pupil miosis is from about 1.50 to about 1.70 millimeters and wherein the duration of the miotic effect is at least about 9 hours.

The present invention is further directed to a method of inducing pupil miosis comprising administering to a subject in need thereof a pharmaceutically effective amount of an ophthalmological composition of the present invention, wherein the pupil miosis is from about 1.50 to about 2.50 millimeters and wherein the duration of the miotic effect is at least about 9 hours.

The present invention is further directed to a method of inducing pupil miosis comprising administering to a subject in need thereof a pharmaceutically effective amount of an ophthalmological composition of the present invention, wherein the pupil miosis is from about 1.80 to about 2.00 millimeters and wherein the duration of the miotic effect is at least about 4 hours.

The present invention is further directed to a method of inducing pupil miosis comprising administering to a subject in need thereof a pharmaceutically effective amount of an ophthalmological composition of the present invention, wherein the pupil miosis is from about 1.80 to about 2.00 millimeters and wherein the duration of the miotic effect is at least about 6 hours.

The present invention is further directed to a method of inducing pupil miosis comprising administering to a subject in need thereof a pharmaceutically effective amount of an ophthalmological composition of the present invention, wherein the pupil miosis is from about 1.80 to about 2.00 millimeters and wherein the duration of the miotic effect is at least about 7.5 hours.

The present invention is further directed to a method of inducing pupil miosis comprising administering to a subject in need thereof a pharmaceutically effective amount of an ophthalmological composition of the present invention, wherein the pupil miosis is from about 1.80 to about 2.00 millimeters and wherein the duration of the miotic effect is at least about 9 hours.

The present invention is further directed to a method of inducing pupil miosis of about 1.35 to 2.0 mm without accommodation, or with minimal accommodation of about 0.50 diopters or less, such that depth of focus enhancement is achieved without noticeable loss of distance vision or other degradation in distance vision quality.

The present invention is further directed to a method of inducing pupil miosis of about 1.50 to 2.4 mm with clinically negligible accommodation, such that depth of focus enhancement is achieved without noticeable loss of distance vision or other degradation in distance vision quality, and a peak minimum pupil diameter typically about 30 to 60 minutes after instillation may be modulated by addition of a cycloplegic agent without induction of irregular astigmatism, pupil mydriasis (i.e. dilation of the radial muscle of the iris), or substantial loss of duration of effect.

The present invention is further directed to a method of improving vision in a subject with ammetropia (vision abnormality), comprising administering to a subject in need thereof a pharmaceutically effective amount of a composition of the present invention.

The present invention is further directed to a method of improving vision in a subject with ammetropia, comprising administering to a subject in need thereof a pharmaceutically effective amount of a composition of the present invention, wherein ammetropia is selected from the group consisting of nearsightedness, farsightedness, regular astigmatism, irregular astigmatism and high degrees of regular astigmatism.

The present invention is further directed at eliminating optical aberrations induced by corneal irregularity, opacities, or very high degrees of regular astigmatism that include regions adjacent or peripheral to the central 1.5 mm optical zone, and thereby inducing improved visual acuity and quality of vision by filtering out these aberrant optics in those suffering from irregular astigmatism or high degrees of more regular astigmatism, such as occurs in conditions such as keratoconus, photorefractive keratectomy induced corneal haze, diffuse lamellar keratitis ("DLK") (post-lasik DLK), other iatrogenic corneal induced irregularity such as cataract incision, glaucoma filtering blebs, implanted glaucoma valves, corneal inlays with or without removal, ectasia post corneal surgery (lasik), and secondary to infection.

The present invention is further directed at improving acuity relative to existing uncorrected refractive error. Upon this improved acuity, patients now requiring toric contact lenses for astigmatism with reduced comfort and optics that may shift during each blink may in many cases require only non-toric soft contact lenses or no contact lenses. Further, those requiring gas permeable contact lenses may no longer require contact lenses or only require much more comfortable soft contact lenses. Patients with high degrees of astigmatism may now require no correction or reduced astigmatic correction. Patients with small to moderate degrees of nearsightedness may require less correction or no longer require correction. Patients with small to moderate degrees of hyperopia (far-sightedness) may require no correction or reduced correction.

The present invention is directed to methods and ophthalmological compositions for improving eye sight. In a preferred embodiment the present invention is directed to methods and ophthalmological compositions for the treatment of presbyopia. In a more preferred embodiment the present invention is directed to ophthalmological compositions comprising aceclidine. In a yet more preferred embodiment present invention is directed to ophthalmological compositions comprising aceclidine and a low-dose cycloplegic agent. In a most preferred embodiment the present invention is directed to ophthalmological compositions comprising aceclidine, a low-dose cycloplegic agent and a combination of inactive ingredients that make effective and/or enhance aceclidine.

BRIEF DESCRIPTION OF THE FIGURES

FIG. 1 is a graphical representation of the effects of pilocarpine and aceclidine with or without tropicamide and with or without a carrier on near and distance vision in a patient over the age of 45.

DETAILED DESCRIPTION OF THE INVENTION

The present invention is directed to compositions and methods of treating presbyopia, irregular astigmatism, and/or refractive error, comprising administering to a patient in need thereof a pharmaceutical composition comprising a muscarinic agonist that preferentially activates M1 and M3 muscarinic acetylcholine receptors, preferably activate M1 more than M3 and most preferably aceclidine or its derivatives. Aceclidine has been surprisingly and unexpectedly discovered to provide enhanced presbyopic reversal with negligible side effects day or night (when viewing includes one or more direct or reflected light sources) using compositions of the present invention.

The compositions and methods of the present invention treat presbyopia by improving depth of focus in patients with presbyopia by administering an ophthalmological composition to the eye that reduces pupil dilation in the dark or in dim light, produces a particular degree and duration of miosis without accommodation, provides cosmetic whitening and/or induce redness prophylaxis. The compositions and methods of the present invention also do not cause significant pupil rebound, tachyphylaxis, ciliary spasms, induction of myopia or reduction in distance vision. Additionally, the compositions and methods of the present invention allow for the further improvement in visual acuity and depth perception of binocular (both eyes) treatment. The ophthalmological composition of the present invention surprisingly creates a pupil of from about 1.5 to about 2.4 mm at the anterior iris plane and about 2.0 mm at the corneal surface with negligible increase in accommodative tone and with a reduction or ablation of the redness that is otherwise a hallmark of the use of miotic agents. This pupil miosis with greatly diminished or absent accommodative tone is superior to the pinhole effect of the Kamra® and Flexivue Microlens® corneal inlays. Pupil miosis is superior because the constriction of the actual pupil does not result in the attendant severe night vision disturbance caused by the light scattering borders of the pre-corneal pinholes created by the inlays. Further pupil miosis provides a greater field of vision and transmission of more focused light. The use of aceclidine has a minimal effect on the longitudinal ciliary muscle, thus reducing risk of retinal detachment when compared to the use of general muscarinic agonists such as pilocarpine and carbachol. The further inclusion of a cycloplegic agent resulted in only 0.04 mm of anterior chamber shallowing. Aceclidine particularly as enhanced for the present invention also has greater magnitude, duration, and control of minimum pupil diameter. Compositions of the present invention achieve these advantages while having negligible effects on accommodation, thus avoiding the distance blur typically seen in patients as a response to pilocarpine and/or carbachol induced miosis. Any effects on accommodation may be further reduced or totally eliminated in preferred embodiments with a cycloplegic agent. Aceclidine is capable of producing the increased depth of focus by pupil miosis described in the present invention without the need of a selective α-2 adrenergic receptor agonist ("α-2 agonist"). Particularly enhanced miosis occurs with use of compositions of the present invention, thus making it possible to use an α-2 agonist at low concentrations to reduce eye redness. Further, due to the apparent and surprisingly selective nature of aceclidine, administration to the eye almost exclusively affects pupil miosis rather than ciliary muscle contraction. Thus, the administration of aceclidine results in pupil miosis without accommodation and attendant distance blur. However, aceclidine may cause some redness and brow ache, and without formulation enhancement of the present invention may produce less than optimal pupil miosis or at extremely high concentration more than desired peak miosis with added dimming of vision in dim or absent lighting.

Certain embodiments of the present invention enhance the discovered preferred degree of pupillary miosis by providing a consistent range of effect of about 1.50-2.20 mm for most patients using a preferred embodiment of a nonionic surfactant and viscosity enhancer. Similar benefit may be achieved using other permeation enhancers, particularly Carbopol® (polyacrylic acid), and various viscosity additives that increase drug residence time, such as xanthan gums, guar gum, alginate, and other in situ gels well known to experts in the art. The present invention further prevents nasal congestion otherwise occurring when substantial aceclidine levels reach the nasal mucosa, due to the rheologic properties of the preferred embodiment.

The combination of aceclidine and a low concentration of a selective α-2 adrenergic receptor agonist (α-2 agonist or α-2 adrenergic agonist), such as fadolmidine, brimonidine or guanfacine, allows for the desired miotic effect with diminished or no redness. The use of low concentrations of a selective α-2 agonist results in substantial reduction of hyperemia with greatly reduced risk of rebound hyperemia that is found in concentrations of about 0.06% w/v or more. Furthermore, the use of low concentrations of selective α-2 agonist does not adversely modify the pupil constriction caused by aceclidine. In contrast, the use of brimonidine 0.20% w/v, when topically applied for pupil modulation for night vision, result in tachyphylaxis of pupil modulation due to α-2 receptor upregulation in almost 100% of treated subjects within four weeks of use.

Unexpectedly, the addition of a cycloplegic agent results in reduction of any brow ache or associated discomfort by further reducing the degree of ciliary spasms on instillation without impairing the miotic response. This lack of impairment of the miotic response is an unexpected surprising discovery, as particular cycloplegic agents, such as tropicamide, have known pupil dilating effects at concentrations as low as 0.01% w/v (Grünberger J. et al., The pupillary response test as a method to differentiate various types of dementia, Neuropsychiatr, 2009, 23(1), pg 57). More specifically cycloplegic agents cause pupil mydriasis (i.e. dilation of the radial muscle of the iris). Further, the addition of a cycloplegic agent to the miotic agent unexpectedly increases the time at which the pupil maintains the desired size range without becoming too restricted. Peak miotic effect at 30-60 minutes can be titrated in inverse relation to the cycloplegic concentration. The concentrations of tropicamide discovered in the present invention apparently cause more relaxation of the ciliary muscle than the iris radial musculature. In fact, iris mydriasis is discovered to be suppressed by the addition of tropicamide to compositions containing concentrations of aceclidine used in the present invention, with instead a more consistent level of miosis for the duration of the miotic effect. Additionally and quite surprisingly, unexpectedly, and beneficially the addition of tropicamide can reduce the degree of peak pupil miosis without inducing mydriasis thereby creating a more constant and ideal pupil size throughout the drug induced miosis. This more consistent pupil size allows for beneficial near and distance vision without the adverse dimming or loss of resolution due to diffraction limits at the very reduced pupil sizes seen at peak pupil miosis (e.g. 1.25 mm).

General miotic agents, such as pilocarpine, carbachol and phospholine diesterase, are capable of causing pupil miosis resulting in improved near vision of presbyopic patients. However, there is an inverse reduction in distance vision associated with these general miotic agents from miosis at peak effect and accommodation that is not seen with aceclidine. The co-administration of a cycloplegic agent with aceclidine surprisingly results in an attenuation of this reduction in distance vision.

Comfort, safety, and efficacy of a preferred embodiment of an ophthalmological composition of the present invention results from the presence of a nonionic surfactant, such as cyclodextrin alpha, beta, or gamma chains, preferably 2-hydroxypropyl beta-cyclodextrin ("HPβCD"), and or sulfobutyl ether derivative of β-cyclodextrin (Captisol®), polyoxyl 40 stearate or poloxamer 407; a viscosity enhancing agent, such as carboxymethyl cellulose ("CMC"); a tonicity adjustor, such as sodium chloride; a preservative, such as benzalkonium chloride and a pH from about 5.0 to about 8.0. Further, an increase in the concentration of the viscosity agent and the electrolyte may result in reduced redness. Specifically, increasing CMC from 0.50% to 0.75% w/v (preferably 0.80% w/v) and sodium chloride from 0.25% to 0.50% w/v results in reduced redness.

DEFINITIONS

As used herein, the term "composition" is intended to encompass a product comprising the specified ingredients in the specified amounts, as well as any product which results, directly or indirectly, from a combination of the specified ingredients in the specified amounts.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

The term muscarinic receptor agonist ("muscarinic agonist") encompasses agonists that activate muscarinic acetylcholine receptors ("muscarinic receptors"). Muscarinic receptors are divided into five subtypes named M1-M5. Muscarinic agonists of the present invention include those muscarinic agonists that preferentially activate M1 and M3 receptors over M2, M4 and M5 receptors ("M1/M3 agonists"). M1/M3 agonists include but are not limited to aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxasdiazol-5-yl]-1,4,5,6-tetrahydropyrimidine hydrocholoride), N-arylurea-substituted 3-morpholine arecolines, VUO255-035 (N-[3-oxo-3-[4-(4-pyridinyl)-1-piperazinyl]propyl]-2,1,3-benzothiadiazole-4-sulfonamide), benzylquinolone carboxylic acid (BQCA), WAY-132983, AFB267B (NGX267), AC-42, AC-260584, chloropyrazines including but not limited to L-687, 306, L-689-660, 77-LH-28-1, LY593039, and any quiniclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof. A preferred M1/M3 agonist is aceclidine. In a preferred embodiment, muscarinic agonist of the present invention include those muscarinic agonist that preferentially activate M1 and M3 over M2, M4, and M5; and even more preferably activate M1 over M3. In a more preferred embodiment muscarinic agonist of the present invention include those muscarinic agonist that only activate M1.

The term "aceclidine" encompasses its salts, esters, analogues, prodrugs and derivatives including, but not limited to, aceclidine as a racemic mixture, aceclidine (+) enantiomer, aceclidine (−) enantiomer, aceclidine analogues, including, but not limited to, highly M1 selective 1,2,5 thiadiazole substituted analogues like those disclosed in Ward. J. S. et al., 1,2,5-Thiadiazole analogues of aceclidine as potent m1 muscarinic agonists, *J Med Chem,* 1998, Jan. 29, 41(3), 379-392 and aceclidine prodrugs including but not limited to carbamate esters.

The term "selective α-2 adrenergic receptor agonists" or "α-2 agonist" encompasses all α-2 adrenergic receptor agonists which have a binding affinity of 900 fold or greater for α-2 over α-1 adrenergic receptors, or 300 fold or greater for α-2a or α-2b over α-1 adrenergic receptors. The term also encompasses pharmaceutically acceptable salts, esters, prodrugs, and other derivatives of selective α-2 adrenergic receptor agonists.

The term "low concentrations" or "low-dose" refers to concentrations from between about 0.0001% to about 0.065% w/v; more preferably, from about 0.001% to about 0.035% w/v; even more preferably, from about 0.01% to about 0.035% w/v; and even more preferably, from about 0.03% to about 0.035% w/v.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, and Alphagan®.

The terms "treating" and "treatment" refer to reversing, alleviating, inhibiting, or slowing the progress of the disease, disorder, or condition to which such terms apply, or one or more symptoms of such disease, disorder, or condition.

The term "pharmaceutically acceptable" describes a material that is not biologically or otherwise undesirable (i.e. without causing an unacceptable level of undesirable biological effects or interacting in a deleterious manner).

As used herein, the term "pharmaceutically effective amount" refers to an amount sufficient to effect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, a "pharmaceutically effective amount" will depend upon the context in which it is being administered. A pharmaceutically effective amount may be administered in one or more prophylactic or therapeutic administrations.

The term "prodrugs" refers to compounds, including, but not limited to, monomers and dimers of the compounds of the invention, which have cleavable groups and become, under physiological conditions, compounds which are pharmaceutically active in vivo.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, hyaluronic acid, malic acid, sulphuric acid and phosphoric acid and such organic acids as oxalic acid, malic acid, maleic acid, methanosulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, a heteroaryl group or other suitable substituent.

Compositions of the Invention

In one embodiment, the present invention is directed to an ophthalmological composition comprising aceclidine. In a preferred embodiment, aceclidine is at a concentration from about 0.25% to about 2.0% w/v, more preferably from about 0.50% to about 1.90% w/v, still more preferably from about 1.25% to about 1.85% w/v, and most preferably from about 1.35% to about 1.65% w/v. As aceclidine is a tertiary amine with asymmetry, both a + and − optical isomer exist (where in some studies (+) is more potent and in others it is felt (−) may be more potent). For the above concentrations polarimetry demonstrated an exactly equal ratio of (+) and (−) isomer for these concentrations. Altering this ratio could therefore alter this concentration range proportional to a change in ratio.

The present invention is further directed to an ophthalmological composition comprising a muscarinic agonist, preferably a nonionic surfactant above its critical micellar concentration for the composition, and a viscosity enhancing agent; or alternatively an in situ gelling agent. In preferred embodiments the initial viscosity of the composition on topical application is above 20 cps, preferably 50 cps, and more preferably above 70 cps at low shear (1/s).

Nonionic surfactants suitable for the present invention include cyclodextrins, polyoxyl alkyls, poloxamers or combinations thereof, and may include in addition combinations with other nonionic surfactants such as polysorbates. Preferred embodiments include polyoxyl 40 stearate and optionally Poloxamer 188, Poloxamer 407, Polysorbate 20, Polysorbate 80, ionically charged (e.g. anionic) beta-cyclodextrins with or without a butyrated salt (Captisol®) 2-hydroxypropyl beta cyclodextrin ("HPβCD"), alpha cyclodextrins, gamma cyclodextrins, Polyoxyl 35 castor oil, and Polyoxyl 40 hydrogenated castor oil or combinations thereof. Further, substitution of other nonionic surfactants compatible with ophthalmological use allows for similar formulation advantages, which may included but is not limited to one or more of a nonionizing surfactant such as poloxamer, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxyl, polyoxyl stearate, nonoxynol, octyphenol ethoxylates, nonyl phenol ethoxylates, capryols, lauroglycol, PEG, Brij® 35(polyoxyethyleneglycol dodecyl ether; Brij is a registered trademark of Uniqema Americas LLC), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris (hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl)methyl-2-aminoethane sulfonic acid (TES), 2-Amino-2-hydroxymethyl-propane-1,3-diol (Tris), tyloxapol, and Span® 20-80 (sorbitan monolaurate, sorbitan monopalmitate, sorbitan monostearate, and sorbitan monooleate). In certain embodiments the addition of an anionic surfactant such as sodium lauryl sulfate and or sodium ester lauryl sulfate may be preferred.

Ophthalmological in situ gels which may be substituted for or added in addition to one or more nonionic surfactants include but are not limited to gelatin, carbomers of various molecular weights including carbomer 934 P and 974 P, xanthan gums, alginic acid (alginate), guar gums, locust bean gum, chitosan, pectins and other gelling agents well known to experts in the art.

In preferred embodiments the nonionic surfactant is polyoxyl 40 stearate at a concentration from about 1 to about 15% w/v, more preferably at about 5.5% w/v.

In such preferred embodiment, polyoxyl 40 stearate is found to enhance the redness reduction effect preferentially over aqueous solutions and other nonionic surfactants such as poloxamer 407, particularly in the presence of an α-2 agonist.

Viscosity enhancers suitable for the present invention include, but are not limited to, carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxyethyl cellulose, or hydroxyethyl cellulose, hyaluronic acid, dextran, polyethylene glycol, polyvinyl alcohol, polyvinyl pyrrolidone, gellan, carrageenan, alignic acid, carboxyvinyl polymer or combinations thereof. In a preferred embodiment the viscosity enhancer will have an equilibration viscosity between 10 centipoise ("cps") and 100 cps between eyelid blinks and 30 cps or less, preferably 20 cps or less and more preferably 15 cps or less during an eyelid blink. In a preferred embodiment the viscosity enhancer is 0.62% to 1.25% w/v CMC, more preferably from 0.75% to 0.87% w/v CMC (1%=2,500 centipoise), and most preferably 0.80% w/v CMC (1% in water=2,500 centipoise).

Not wishing to be held to particularly theory, it appears the combination of nonionic surfactant and viscosity enhancer results in nanometer diameter particles that are, for example, spheroid, other geometric shaped rods or ellipsoids, that aggregate such as in bilayers. These particles are at low surface tension and may be at relatively high viscosity, both allowing prolonged residence time with minimal flow with tears exiting the lacrimal puncta thus allowing better penetration of the tear mucosal layer and cornea and reduced nasal mucosal penetration and local effect as well as reduced systemic absorption. Once applied topically an initial viscosity well above 20 cps prevents nasolacrimal drainage and nasal congestion from the aceclidine, which is a direct vasodilating cholinergic drug and may otherwise cause some degree of nasal congestion. This comfort is achieved without systemic side from nasolacrimal vascular entry into the circulation, suppressing direct effects on nasal mucosa leading to nasal congestion as results from aceclidine aqueous compositions.

The selective α-2 agonist may be included within the composition of the present invention or applied topically preferably just minutes before or less preferably just minutes afterward if additional means to reduce nasal congestion or redness is desired for sensitive subjects. Selective α-2 agonists suitable for the present invention have minimal α-1 agonist activity at low concentrations. For example, for brimonidine or fadolmidine, 1% to 2% w/v is considered extremely high, 0.5% to 1.0% w/v still highly inductive of a-1 receptors and toxic for purposes of the present invention. Further, 0.10% to 0.5% w/v is still too high and even 0.070% to 0.10% w/v is associated with a higher than preferred incidence of rebound hyperemia (however, for dexmedetomidine, its greater lipophilicity and intraocular penetration reduces rebound risk in this range). Only 0.065% w/v or below is potentially acceptable, where for most α-2 agonists, depending on degree of selectivity 0.050% w/v or even more preferably 0.035% w/v or less is desired. On the other hand some degree of useful activity may occur at one or more orders of magnitude further reduction of concentration. The preferred embodiments, brimonidine, fadolmidine and guanfacine, of the present invention preferentially stimulate α-2 adrenergic receptors, and even more preferably α-2b adrenergic receptors so that α-1 adrenergic receptors are not stimulated sufficiently enough to cause excessive large vessel arteriolar constriction and vasoconstrictive ischemia. In addition, it has been discovered that preventing or reducing redness for drugs that otherwise directly induce redness, such as the acetylcholine agonist, aceclidine, enhances compliance for sensitive subjects that may have induced redness or nasal congestion even with formulations of the present invention that do not include an α-2 agonist. However, because α-2 agonists are shifted to their ionized equilibrium an acidic pH is somewhat offset by the fact such agonists exert greater affect at neutral or alkaline pH. Therefore each α-2 agonist has a preferred pH range depending on its lipophilicity and pKa value when added to the inventive compositions with aceclidine. For the present invention while pH range of 5.0 to 8.0 is tolerated, preferred embodiments are at pH 5.5 to 7.5 and more preferably 6.5 to 7.0. Further, it has been discovered that cyclodextrins and/or polyoxyl 40 stearate as a nonionic surfactant component or as the sole nonionic surfactant, result in a greater whitening effect when the α-2 agonist is included in the composition rather than poloxamer 407. The α-2 agonist may optionally be applied separately or in certain preferred embodiments with formulations of the present invention that do not include an α-2 agonist, such as those formulas with polyoxyl 40 stearate 5.5% w/v as the non-ionic surfactant, although the α-2 agonist is not required except for occasional sensitive subjects. Fadolmidine represents the α-2 agonist with highest hydrophilicity and therefore high surface retention for the present invention. Guanfacine is also highly selective and hydrophilic. Brimonidine is highly selective with moderate lipophilicity. Finally, dexmedetomidine has high selectivity with high lipophilicity that may be used with less efficacy for reducing redness for the purposes of the present invention (although possibly inducing fatigue as a side effect in some patients). In a preferred embodiment using polyoxyl 40 stearate 5.5% w/v; CMC 0.80% w/v; NaCl 0.037% w/v; EDTA 0.015% w/v, borate buffer 5 mM and BAK 0.007% w/v results in redness of about 1.0 to 1.5 out of 4 which is transient lasting about ten minutes, and by 30 minutes returns to about baseline.

In one embodiment, the selective α-2 adrenergic receptor agonist is a compound which has binding affinity of about 900 fold or greater, even more preferably about 1000 fold or greater, and most preferably, about 1500 fold or greater.

The selective α-2 adrenergic receptor agonist may be present at a concentration from between about 0.0001% to about 0.065% w/v; more preferably, from about 0.001% to about 0.035% w/v; even more preferably, from about 0.01% to about 0.035% w/v; and even more preferably, from about 0.020% to about 0.035% w/v.

In one embodiment, the selective α-2 adrenergic receptor is selected from the group consisting of brimonidine, guanfacine, fadolmidine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds. Analogues of these compounds that function as highly selective α-2 agonists may also be used in compositions and methods of the present invention.

In a more preferred embodiment, the selective α-2 agonist is selected from the group consisting of fadolmidine, guanfacine and brimonidine. In a yet more preferred embodiment the selective α-2 agonist is brimonidine in the form of a salt at a concentration of 0.025% to 0.065% w/v, more preferably from 0.03% to 0.035% w/v. In a preferred embodiment, the salt is a tartrate salt.

In another yet more preferred embodiment, the selective α-2 agonist is fadolmidine at a concentration from about 0.005% to about 0.05% w/v, more preferably from 0.02% to about 0.035% w/v in the form of a hydrochloride ("HCl") salt.

In another yet more preferred embodiment, the selective α-2 agonist is guanfacine at a concentration from about 0.005% to about 0.05% w/v, more preferably from 0.02% to about 0.035% w/v in the form of an HCl salt.

In another yet more preferred embodiment, the selective α-2 agonist is dexmedetomidine at a concentration from about 0.005% to about 0.05% w/v, more preferably from 0.04% to about 0.05% w/v in the form of an HCl salt.

In another preferred embodiment a pH less than physiologic pH is found to enhance the whitening effect for brimonidine, preferably pH 4.5 to 6.5, and more preferably pH 5.5 to 6.0. However, redness reduction is achieved at all pHs, and enhancement of aceclidine absorption occurs at alkaline pH, such that more effect occurs from a given concentration, and therefore while effective at pH ranges from 4.5 to 8.0, pH range of 6.5 to 7.5 is preferred for the present invention, and 7.0 to 7.5 most preferred.

The present invention is further directed to an ophthalmological composition further comprising a cycloplegic agent. It is a surprising and totally unexpected discovery of the present invention that certain cycloplegic agents can be combined with miotic agents, particularly for the present invention, aceclidine, without reducing miotic onset, magnitude, or duration; and further blunt the normally attendant spike in miotic effect coinciding with time of peak absorption in aqueous formulations to provide a constant miosis versus time after onset from 15 to 30 minutes to 6 to 10 hours depending on the desired formulation. The addition of the cycloplegic agent also reduces any residual associated discomfort that may otherwise occur soon after instillation, which presumably is a result of ciliary spasms or excessive pupillary miosis.

Cycloplegic agents suitable for the present invention include, but are not limited to, atropine, Cyclogyl® (cyclopentolate hydrochloride), hyoscine, pirenzepine, tropicamide, atropine, 4-diphenylacetoxy-N-methylpiperidine methobromide (4-DAMP), AF-DX 384, methoctramine, tripitramine, darifenacin, solifenacin (Vesicare), tolterodine, oxybutynin, ipratropium, oxitropium, tiotropium (Spriva), and otenzepad (a.k.a. AF-DX 116 or 11-{[2-(diethylamino) methyl]-1-piperidinyl } acetyl]-5,11dihydro-6H-pyrido [2,3b] [1,4]benzodiazepine-6-one). In a preferred embodiment the cycloplegic agent is tropicamide at a concentration from about 0.01% to about 0.10% w/v, more preferably from about 0.025% to about 0.080% w/v and still more preferably from about 0.04% to about 0.06% w/v. In another preferred embodiment the cycloplegic agent is a mixture of tropicamide at a concentration from about 0.04% to about 0.07% w/v or pirenzepine or otenzepad at a concentration from about 0.002% to about 0.05% w/v.

In a preferred embodiment, tropicamide 0.01% w/v was found to slightly reduce brow ache, 0.030% w/v to further reduce brow ache and from 0.04% to about 0.07% w/v to completely eliminate brow ache without reduction of the average pupillary miosis diameter over duration of effect. Tropicamide in preferred embodiments has demonstrated completely unexpected sensitivity of effect, where at about 0.04% w/v unexpectedly and very effectively reduces or eliminates brow ache and ciliary spasm pain, becoming very noticeably further reduced at 0.042% w/v and absent at 0.044% w/v in a preferred embodiment with no cycloplegia (surprising due to its common use as a pupil dilating agent). Yet, tropicamide did not reduce the mean degree of pupil miosis, the time of onset of pupil miosis or the subsequent visual benefits. On the contrary, tropicamide blunted the peak miosis seen in aqueous formulations to create a smooth consistent miotic effect over time. It allowed modulation of peak pupil miosis to achieve a more even effect over time with no dilation as has been found with its prior use. Specifically, tropicamide is useful to prevent transient constriction below 1.50 mm at 30 to 60 minutes following aceclidine in some embodiments and to reduce transient excessive and undesirable dimming of vision that may otherwise occur at peak onset of about 30 minutes. As an example, an ophthalmological composition comprising 1.53% w/v aceclidine, 5% w/v HPβCD, 0.75% w/v CMC, 0.25% w/v NaCl, 0.01% w/v BAK and a phosphate buffer at pH 7.0; or 1.45% w/v aceclidine; 5.5% w/v polyoxyl 40 stearate; 0.80% w/v CMC; 0.037% w/v NaCl; 0.015% w/v EDTA; 0.007% w/v BAK and 5 mM phosphate buffer at a pH 7.0; was varied from 0.040% w/v tropicamide, where moderate dimming was noted, to 0.044% w/v tropicamide where dimming became almost undetectable other than in extremely dim light conditions. This additional pupil size modulation with a cycloplegic agent allows aceclidine concentrations sufficient for prolonged effect while blunting the attendant peak excessive constriction that is undesirable as well as any uncomfortable brow ache. Surprisingly and due to its short-acting nature, tropicamide achieves this blunting effect without causing mydriasis. Further, in a preferred embodiment, tropicamide 0.014% w/v was found to reduce brow ache, 0.021% w/v to further reduce brow ache and from 0.028% to 0.060% w/v and in some embodiments up to 0.09% w/v to completely eliminate brow ache without cycloplegia (i.e. paralysis of ciliary muscle of the eye).

It has been found for a racemic 50:50 mixture of (+) and (−) aceclidine optical isomers (where in some studies (+) is more potent and in others it is felt (−) may be more potent) tropicamide effects may vary depending on the ratio of aceclidine to tropicamide. For example, in an ophthalmological composition of the present invention comprising 1.55% w/v aceclidine, 5.5% w/v HPβCD or in a preferred embodiment polyoxyl 40 stearate, 0.75% w/v CMC (1%=2,500 centipoise), 0.25% w/v NaCl, and 0.01% w/v BAK and at pH 7.5, 0.042% w/v tropicamide can be differentiated from even 0.035% w/v, with the former demonstrating normal indoor night vision and the latter slight dimming that becomes more noticeable at still lower concentrations. At higher concentrations, such as from about 0.075% to about 0.090% w/v tropicamide, loss of optimal range pupil constriction 1.50 mm to 1.80 mm range begins, and frank mydriasis at higher concentrations begins to occur. As isomer ratio may alter the effective concentration, this must be factored into the clinical efficacy anticipated using aceclidine; for preferred embodiments of the present invention a polarimeter was used to determine an exact 50:50 isomer ratio was used (personal communication Toronto Research Chemicals).

FIG. 1 shows the effect of a miotic agent with or without a cycloplegic agent and with or without a carrier. Subject is an emmetrope over the age of 45 with a baseline near vision of 20.100 and baseline distance vision of 20.20. Topical administration to the eye of 1% w/v pilocarpine in saline solution results in an improvement of near vision to 20.40 (8a), however this improvement comes at the expense of a reduction in distance vision to 20.100 (8b). The addition of 0.015% w/v tropicamide results in an improvement of near vision to 20.25 (9a) and a lessening of the reduction of distance vision to 20.55 (9b), though in certain instances with some induced irregular astigmatism (mildly blotched areas in reading field of vision). Topical administration of 1.55% w/v aceclidine in saline solution results in an improvement of near vision to 20.40 for an extended time period of 6 hrs (10a) without any effect on the baseline distance vision (10b). 10c and 10d show the effects of administering aceclidine in a carrier composed of 5.5% w/v 2-hydroxypropyl beta cyclodextrin, 0.75% w/v CMC (1%=2,500 centipoise), 0.25% w/v NaCl, and 0.01% w/v BAK. As seen in 10c the carrier increases the beneficial effect of aceclidine resulting in better than 20.20 near vision. As seen in 10d a similar increase in distance vision occurs. 10e and 10f show the effects of adding 0.042% w/v tropicamide to the aceclidine in the carrier. As seen in 10e near vision is improved to 20.15 with a quicker onset of maximum visual acuity. As seen in 10f a similar improvement is seen in distance vision. Taken together, FIG. 1 shows that aceclidine is capable of temporarily correcting near vision in a presbyopic subject without affecting the baseline distance vision. Similar results can be achieved with a different miotic agent, pilocarpine, with the addition of a cycloplegic agent such as tropicamide. A proper drug carrier can also have a beneficial effect.

The present invention is further directed to an ophthalmological composition further comprising a tonicity adjustor and a preservative.

A tonicity adjustor can be, without limitation, a salt such as sodium chloride ("NaCl"), potassium chloride, mannitol or glycerin, or another pharmaceutically or ophthalmologicalally acceptable tonicity adjustor. In certain embodiments the tonicity adjustor is 0.037% w/v NaCl, Preservatives that can be used with the present invention include, but are not limited to, benzalkonium chloride ("BAK"), chlorobutanol, thimerosal, phenylmercuric acetate, disodium ethylenediaminetetraacetic acid, phenylmercuric nitrate, perborate or benzyl alcohol. In a preferred embodiment the preservative is BAK at a concentration of about 0.001% to about 1.0% w/v, more preferably at a concentration of about 0.007% w/v. In another preferred embodiment the preservative is perborate at a concentration of 0.01% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, phosphate buffers and borate buffers. It is understood that acids or bases can be used to adjust the pH of the composition as needed, preferably of 1 to 10 mM concentration, and more preferably about 5 mM. In a preferred embodiment the pH is from about 4.0 to about 8.0, in a more preferred embodiment the pH is from about 5.0 to about 7.0.

The present invention is further directed to an ophthalmological composition further comprising an antioxidant. Antioxidants that can be used with the present invention include but are not limited to disodium ethylenediaminetetraacetic acid at a concentration from about 0.005% to about 0.50% w/v, citrate at a concentration from about 0.01% to about 0.3% w/w, dicalcium diethylenetriamine pentaacetic acid ("Ca2DTPA") at a concentration from about 0.001% to about 0.2% w/v, preferably about 0.01% w/v Ca2DTPA which can be formulated by adding 0.0084% w/v Ca(OH)$_2$ and 0.0032% w/v pentetic acid to the formulation and mixing slowly. Further combinations of antioxidants can be used. Other antioxidants that can be used with the present invention include those well known to experts in the art such as ethylenediaminetetraacetic acid at a concentration from about 0.0001% to about 0.015% w/v.

It is a surprising and unexpected discovery that topical formulations of the present invention, particularly one of the preferred embodiments comprising aceclidine 1.35% to 1.55% w/v; 5.5% w/v polyoxyl 40 stearate; 0.80% w/v CMC; 0.037% w/v NaCl; 0.015% w/v EDTA; 0.007% w/v BAK; and 5mM phosphate buffer at pH 7.0 result in considerably prolonged contact lens wear and comfort after a single instillation daily. The single daily use of the preferred embodiments allowed a subject with dry eye to sleep in his lenses for one week periods where previously even after a single night vision would be blurred and contact lenses coated with film requiring removal and cleaning or replacement (see Example 7).

The following representative embodiments are provided solely for illustrative purposes and are not meant to limit the invention in any way.

Representative Embodiments

In certain embodiments, the present invention is directed to compositions and methods for the treatment of presbyopia comprising a muscarinic agonist of Formula I:

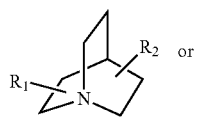

Formula II:

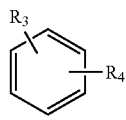

wherein:
R₁ is H, O, CH₃, an alkyl, acetyl, acyl, an aziridine, nitrile, imine, nitryl-imine methyl substitution, nitryl-imine methyl substitution with ester attached, an aromatic ring, a substituted aromatic ring, an azide, acetamide, a pyridine, a substituted pyridine, a pyrollidine, a substituted pyrollidine, imidazole, a substituted imidazole, an imidazole wherein one or more carbon atoms are replaced by O or S, a substituted imidazole wherein one or more carbon atoms are replaced by O or S, a benzimidazole, a substituted benzimidazole, a benzimidazole wherein one or more carbon atoms are replaced by O or S, or a substituted benzimidazole wherein one or more carbon atoms are replaced by O or S;

R₂ is H, O, CH₃, an alkyl, acetyl, acyl, nitrile, imine, nitryl-imine methyl substitution, or an ester-O-alkyl;

R₃ is H, CH₃; acyl, acetyl, or ester; and

R₄ is acyl, acetyl, ester, CH₃, an alkyl, an aromatic ring, a substituted aromatic ring, cyclohexane, or a substituted cyclohexane ring, and wherein each of R₁ and R₂ independently substitute for a H of a —CH₂— of the quinuclidine ring.

In certain embodiments, the present invention is directed to compositions and methods for the treatment of presbyopia comprising a muscarinic agonist that preferentially activates M1 and M3 muscarinic acetylcholine receptors.

In certain embodiments, the present invention is directed to compositions and methods for the treatment of presbyopia comprising a muscarinic agonist that activates only M1 muscarinic acetylcholine receptors.

In certain other embodiments, the present invention is directed to an ophthalmological composition for the treatment of presbyopia comprising aceclidine.

In certain other embodiments, the present invention is directed to an ophthalmological composition for the treatment of presbyopia comprising aceclidine and a cycloplegic agent.

In certain other embodiments, the present invention is directed to an ophthalmological composition for the treatment of presbyopia comprising aceclidine, a cycloplegic agent and a selective α-2 adrenergic receptor agonist.

In certain other embodiments, the present invention is directed to an ophthalmological composition for the treatment of presbyopia comprising a general miotic agent and a cycloplegic agent.

In certain other embodiments, the present invention is directed to an ophthalmological composition of the present invention comprising:
a general miotic agent, a compound of Formula I or II, a muscarinic agonist or aceclidine;
optionally a cycloplegic agent;
optionally a selective α-2 adrenergic receptor agonist;
a viscosity enhancer; and
a surfactant selected from the group consisting of an anionic surfactant, a nonionic surfactant, and a combination thereof.

In certain other embodiments, the viscosity enhancer is carboxymethyl cellulose and the anionic surfactant is selected from the group consisting of a gamma cyclodextrin, Captisol® (sulfobutylether β-cyclodextrin), sodium lauryl sulfate and sodium ester lauryl sulfate and the nonionic surfactant is selected from the group consisting of a poloxamer, a polysorbate, Span® 20-80(sorbitan monolaurate, sorbitan monopalmitate, sorbitan monostearate, and sorbitan monooleate), a polyoxyl alkyl, a cyclodextrin and derivatives thereof.

In certain other embodiments, the present invention is directed to an ophthalmological composition of the present invention comprising:
a general miotic agent, a compound of Formula I or II, a muscarinic agonist or aceclidine;
optionally a cycloplegic agent;
optionally a selective α-2 adrenergic receptor agonist; and
a surfactant selected from the group consisting of Captisol® (sulfobutylether β-cyclodextrin), polyoxyl 40 stearate and 2-hydroxypropyl beta-cyclodextrin.

In certain other embodiments, the present invention is directed to an ophthalmological composition of the present invention comprising:
a general miotic agent, a compound of Formula I or II, a muscarinic agonist or aceclidine;
optionally a cycloplegic agent;
optionally a selective α-2 adrenergic receptor agonist;
a surfactant selected from the group consisting of Captisol® (sulfobutylether β-cyclodextrin), polyoxyl 40 stearate and 2-hydroxypropyl beta-cyclodextrin; and
one or more additional non-ionic surfactants selected from the group consisting of poloxamer 188, polyoxyl 40 stearate, polyoxyl 35 castor oil, polysorbate, a Span® 20-80 (sorbitan monolaurate, sorbitan monopalmitate, sorbitan monostearate, and sorbitan monooleate), tyloxapol and combinations thereof.

In certain other embodiments, the present invention is directed to an ophthalmological composition of the present invention comprising:
a general miotic agent, a compound of formula I or II, a muscarinic agonist or aceclidine;
optionally a cycloplegic agent; and
optionally a selective α-2 adrenergic receptor agonist,
wherein the selective α-2 adrenergic receptor agonist is selected from the group consisting of brimonidine, dexmedetomidine, fadolmidine and guanfacine.

In certain other embodiments, the present invention is directed to an ophthalmological composition of the present invention comprising:
a general miotic agent, a compound of Formula I or II, a muscarinic agonist or aceclidine;
optionally a cycloplegic agent; and
optionally a selective α-2 adrenergic receptor agonist,
wherein the cycloplegic agent is selected from the group consisting of pirenzepine, tropicamide, Cyclogyl® (cyclopentolate hydrochloride), 4-diphenylacetoxy-N-methylpiperidine methiodide (4-DAMP), xanomeline, otenzepad and a combination thereof.

In preferred embodiments, a composition of the present invention has a pH greater than or equal to about 5.5

In certain other embodiments the present invention is directed to an ophthalmological composition of the present invention comprising:
  a general miotic agent, a compound of Formula I or II, a muscarinic agonist or aceclidine;
  optionally a cycloplegic agent;
  optionally a selective α-2 adrenergic receptor agonist; and
  an in situ gel selected from the group consisting of Carbopol® (polyacrylic acid) at a concentration from about 0.0001% to about 0.4% w/v, alginate, pectin, xanthan gum and guar gum.

In a preferred embodiment, the ophthalmological composition comprises:
  aceclidine at a concentration of about 1.53% w/v;
  tropicamide at a concentration of about 0.044% w/v;
  carboxymethyl cellulose at a concentration of about 0.80% w/v;
  sodium chloride at a concentration of about 0.75% w/v;
  benzalkonium chloride at a concentration of about 0.01% w/v;
  and phosphate buffer at a concentration of about 5 millimolar,
  wherein the pH is about 8.0.

In another preferred embodiment, the ophthalmological composition comprises:
  aceclidine at a concentration of about 1.53% w/v;
  tropicamide at a concentration of about 0.044% w/v;
  brimonidine at a concentration of about 0.042% w/v;
  carboxymethyl cellulose at a concentration of about 0.80% w/v;
  sodium chloride at a concentration of about 0.75% w/v;
  benzalkonium chloride at a concentration of about 0.01% w/v;
  and phosphate buffer at a concentration of about 5 millimolar,
  wherein the pH is about 8.0.

In a most preferred embodiment, the ophthalmological composition comprises:
  aceclidine at a concentration of about 1.45% w/v;
  tropicamide at a concentration of about 0.044% w/v;
  polyoxyl 40 stearate at a concentration of about 5.5% w/v;
  carboxymethyl cellulose at a concentration of about 0.8% w/v;
  sodium chloride at a concentration of about 0.37% w/v;
  disodium ethylenediaminetetraacetic acid at a concentration of about 0.015% w/v;
  benzalkonium chloride at a concentration of about 0.007% w/v; and
  phosphate buffer at a concentration of about 5 millimolar; and a pH of about 7.0;
where brimonidine 0.40% w/v may be optionally added for slight lessening of transient redness for about the first 10-20 minutes after instillation.

In another embodiment, the ophthalmological composition comprises:
  aceclidine at a concentration of about 1.35% w/v;
  tropicamide at a concentration of about 0.044% w/v;
  Captisol® (sulfobutylether β-cyclodextrin) at a concentration from about 5.0% to about 6.0% w/v;
  carboxymethyl cellulose at a concentration from about 0.90% to about 1.2% w/v;
  sodium chloride at a concentration from about 0.025% to about 0.50% w/v; and
  a buffer at a concentration from about 4.0 millimolar to about 5.0 millimolar selected from the group consisting of phosphate buffer and borate buffer.

In another embodiment, the ophthalmological composition comprises:
  aceclidine at a concentration of about 1.35% w/v;
  tropicamide at a concentration of about 0.044% w/v;
  Captisol® (sulfobutylether β-cyclodextrin) at a concentration from about 5.0% to about 6.0% w/v;
  carboxymethyl cellulose at a concentration from about 0.90% to about 1.2% w/v;
  sodium chloride at a concentration from about 0.025% to about 0.50% w/v, preferably from about 0.037% to about 0.05% w/v;
  optionally, benzalkonium chloride at a concentration of about 0.007% w/v or greater; and
  a buffer at a concentration from about 4.0 millimolar to about 5.0 millimolar selected from the group consisting of phosphate buffer and borate buffer.

In another embodiment, the ophthalmological composition comprises:
  aceclidine at a concentration of about 1.35% w/v;
  tropicamide at a concentration of about 0.044% w/v;
  Captisol® (sulfobutylether β-cyclodextrin) at a concentration from about 5.0% to about 6.0% w/v;
  carboxymethyl cellulose at a concentration from about 0.90% to about 1.2% w/v;
  sodium chloride at a concentration from about 0.025% to about 0.50% w/v;
  mannitol at a concentration of about 4.0% w/v; and
  a buffer at a concentration from about 4.0 millimolar to about 5.0 millimolar selected from the group consisting of phosphate buffer and borate buffer.

In another embodiment, the ophthalmological composition comprises:
  aceclidine at a concentration of about 1.35% w/v;
  tropicamide at a concentration of about 0.044% w/v;
  Captisol® (sulfobutylether β-cyclodextrin) at a concentration from about 5.0% to about 6.0% w/v;
  carboxymethyl cellulose at a concentration from about 0.90% to about 1.2% w/v;
  sodium chloride at a concentration from about 0.025% to about 0.50% w/v;
  an antioxidant selected from the group consisting of disodium ethylenediaminetetraacetic acid at a concentration from about 0.005% to about 0.50% w/v, citrate at a concentration from about 0.01% to about 0.3% w/v, Ca2DTPA at a concentration from about 0.001% to about 0.2% w/v and a combination thereof, preferably ethylenediaminetetraacetic acid at a concentration from about 0.0001% to about 0.015% w/v; and
  a buffer at a concentration from about 4.0 millimolar to about 5.0 millimolar selected from the group consisting of phosphate buffer and borate buffer.

In another embodiment, the ophthalmological composition comprises:
  aceclidine at a concentration of about 1.35% w/v;
  tropicamide at a concentration of about 0.044% w/v;
  Captisol® (sulfobutylether β-cyclodextrin) at a concentration from about 5.0% to about 6.0% w/v;
  carboxymethyl cellulose at a concentration from about 0.90% to about 1.2% w/v;
  sodium chloride at a concentration from about 0.025% to about 0.50% w/v;

an α-2 adrenergic receptor agonist at a concentration from about 0.025% to about 0.045% w/v selected form the group consisting of brimonidine, fadolmidine and guanfacine; and
a buffer at a concentration from about 4.0 millimolar to about 5.0 millimolar selected from the group consisting of phosphate buffer and borate buffer.

In another embodiment, the ophthalmological composition comprises:
aceclidine at a concentration of about 1.35% w/v;
tropicamide at a concentration of about 0.044% w/v;
polyoxyl 40 stearate at a concentration from about 5.0% to about 6.0% w/v;
carboxymethyl cellulose at a concentration of about 0.80% w/v;
sodium chloride at a concentration from about 0.025% to about 0.05% w/v, preferably from about 0.037% to about 0.05% w/v; and
a buffer at a concentration from about 4.0 millimolar to about 5.0 millimolar selected from the group consisting of phosphate buffer and borate buffer.

In another embodiment, the ophthalmological composition comprises:
aceclidine at a concentration of about 1.35% w/v;
tropicamide at a concentration of about 0.044% w/v;
polyoxyl 40 stearate at a concentration from about 1% to 10%, and more preferably, from about 5.0% to about 6.0% w/v;
carboxymethyl cellulose at a concentration of about 0.80% to 0.90% w/v;
sodium chloride at a concentration from about 0.025% to about 0.90%, and more preferably 0.05% w/v;
optionally, cocamidopropyl betaine at a concentration of about 0.1% w/v; and
a buffer at a concentration from about 4.0 millimolar to about 5.0 millimolar selected from the group consisting of phosphate buffer and borate buffer.

In another embodiment, the ophthalmological composition comprises:
aceclidine at a concentration of about 1.35% w/v;
tropicamide at a concentration of about 0.044% w/v;
polyoxyl 40 stearate at a concentration from about 5.0% to about 6.0% w/v;
carboxymethyl cellulose at a concentration of about 0.80% w/v;
sodium chloride at a concentration from about 0.025% to about 0.05% w/v;
benzalkonium chloride at a concentration of about 0.007% w/v; and
a buffer at a concentration from about 4.0 millimolar to about 5.0 millimolar selected from the group consisting of phosphate buffer and borate buffer.

In another embodiment, the ophthalmological composition comprises:
aceclidine at a concentration of about 1.35% w/v;
tropicamide at a concentration of about 0.044% w/v;
polyoxyl 40 stearate at a concentration from about 5.0% to about 6.0% w/v;
carboxymethyl cellulose at a concentration of about 0.80% w/v;
sodium chloride at a concentration from about 0.025% to about 0.05% w/v, preferably from about 0.037% to about 0.05% w/v;
an antioxidant selected from the group consisting of disodium ethylenediaminetetraacetic acid at a concentration from about 0.005% to about 0.50% w/v, citrate at a concentration from about 0.01% to about 0.3% w/w, Ca2DTPA at a concentration from about 0.001% to about 0.2% w/v and a combination thereof, preferably ethylenediaminetetraacetic acid at a concentration from about 0.0001% to about 0.015% w/v; and
a buffer at a concentration from about 4.0 millimolar to about 5.0 millimolar selected from the group consisting of phosphate buffer and borate buffer.

In another embodiment, the ophthalmological composition comprises:
aceclidine at a concentration of about 1.35% to 1.45% w/v;
tropicamide at a concentration of about 0.044% w/v;
polyoxyl 40 stearate at a concentration from about 5.0% to about 6.0% w/v;
carboxymethyl cellulose at a concentration of about 0.80% w/v;
sodium chloride at a concentration from about 0.025% to about 0.05% w/v, preferably from about 0.037% to about 0.05% w/v;
an α-2 adrenergic receptor agonist at a concentration from about 0.025% to about 0.045% w/v selected form the group consisting of brimonidine, fadolmidine and guanfacine; and
a buffer at a concentration from about 4.0 millimolar to about 5.0 millimolar selected from the group consisting of phosphate buffer and borate buffer.

In another embodiment, the ophthalmological composition comprises:
aceclidine at a concentration of about 1.40-1.45% w/v;
tropicamide at a concentration of about 0.044% w/v;
carboxymethyl cellulose at a concentration of about 0.85% w/v;
sodium chloride at a concentration of about 0.75% w/v;
wherein said composition further comprises
borate buffer at a concentration of about 10 millimolar;
benzalkonium chloride at a concentration of about 0.01% w/v,
polyoxyl 40 stearate at a concentration of about 5.5% w/v;
citrate at a concentration of about 0.2% w/v;
wherein the composition is at pH of about 7.0, and
wherein w/v denotes weight by volume.

In another embodiment, the ophthalmological composition comprises:
aceclidine at a concentration of about 1.40 w/v;
tropicamide at a concentration of about 0.044% w/v;
carboxymethyl cellulose at a concentration of about 0.80% to about 0.85% w/v;
sodium chloride at a concentration of about 0.05% w/v;
wherein said composition further comprises
borate buffer at a concentration of about 10 millimolar;
benzalkonium chloride at a concentration of about 0.01% w/v,
polyoxyl 40 stearate at a concentration of about 5.5% w/v;
dicalcium diethylenetriamine pentaacetic acid ("Ca2DTPA") at a concentration from about 0.01% w/v;
wherein the composition is at pH of about 7.0, and
wherein w/v denotes weight by volume.

In another embodiment, the ophthalmological composition comprises:
aceclidine at a concentration of about 0.5% w/v; and
poloxamer 188 at about 0.1% w/v;
poloxamer 407 at about 0.2% w/v;
polyoxyl stearate at about 5% w/v;
polyoxyl 35 castor oil at about 0.25% w/v;
carboxymethyl cellulose at a concentration of about 0.80% to about 0.85% w/v;
sodium chloride at a concentration of about 0.25% w/v;
perborate at a concentration of about 0.02% w/v;
citrate buffer at a concentration of about 15 to about 75 mM;
optionally, guanfacine at a concentration of about 0.03% w/v; and
wherein said composition has a pH of about 5.0 to about 8.0; and preferably, about 5.9 to about 6.2; and
wherein w/v denotes weight by volume.

The following Examples are provided solely for illustrative purposes and are not meant to limit the invention in any way.

EXAMPLES

Example 1

Effect of Aceclidine on Vision of Subjects Aged 47 to 67 Years

Table 1 demonstrates the effect on the near focus ability of presbyopic subjects before and after ophthalmological administration of a composition containing aceclidine. Each composition included aceclidine in the concentrations indicated and 5.5% w/v HPβCD, 0.75% w/v CMC, 0.25% w/v NaCl and 0.01% w/v BAK. Additionally compositions administered to subjects 4 and 5 included 0.125% w/v tropicamide. As aceclidine is an enantiomer, the clinical effectiveness may vary with different ratios. For the present studies a nearly exact 50:50 ratio of stereoisomers was measured as best determined by polarimetry.

TABLE 1

Effects of aceclidine on vision of presbyopic patients.

| | | | | Vision Baseline | | | | Post Gtt 15" | | | | |
|---|---|---|---|---|---|---|---|---|---|---|---|---|
| Date | # | Age | Aceclidine % | R Pre Dist | L Pre Dist | R Pre Near | L Pre Near | R Post Dist | L Post Dist | R Post Near | L Post Near | Effect (h) |
| Aug. 21, 2013 | 1 | 67 | 1.5 | 20.20 | 20.30 | 20.60 | 20.60 | 20.20 | 20.20 | 20.15 | 20.15 | 9.00 |
| Aug. 22, 2013 | 2 | 52 | 1.5 | 20.30 | 20.30 | 20.50 | 20.50 | 20.25 | 20.25 | 20.25 | 20.20 | 8.00 |
| Aug. 23, 2013 | 3 | 61 | 1.5 | 20.40 | 20.30 | 20.60 | 20.50 | 20.20 | 20.25 | 20.15 | 20.15 | 8.00 |
| Aug. 23, 2013 | 4 | 61 | 1.1 | 20.20 | 20.25 | 20.80 | 20.50 | 20.15 | 20.15 | 20.20 | 20.15 | 12.00 |
| Aug. 23, 2013 | 5 | 53 | 1.1 | 20.20 | 20.20 | 20.60 | 20.60 | 20.20 | 20.20 | 20.25 | 20.25 | 7.00 |
| Aug. 24, 2013 | 6 | 47 | 1.5 | 20.25 | 20.25 | 20.100 | 20.100 | 20.20 | 20.20 | 20.15 | 20.15 | 8.00 |
| Aug. 25, 2013 | 7 | 58 | 1.5 | 20.30 | 20.200 | 20.100 | 20.30 | 20.25 | 20.30 | 20.20 | 20.30 | 8.00 |

As seen in Table 1 all subjects had less than perfect near vision (20.20) in both the left and right eye (object at 15 inches from the eye) and most subjects had less than perfect distance vision before administration of the composition. After administration of the composition all subjects experienced an improvement in their near vision that lasted from 7 to 12 hours. Surprisingly, the majority of subjects also experienced improvement of their distance vision for the same time period. Still more surprisingly the improvement in near point was much closer than 16" typically required for comfortable reading, in some cases to about 8.5" more commonly seen in individuals 30 or less. The addition of tropicamide, a cycloplegic agent, had no additive or deleterious effect on vision correction.

Example 2

TABLE 2

Effect of concentration of concentration of aceclidine and tropicamide.

| | #1 | #2 | #3 | #4 | #5 (OD) | #5 (OS) | #6 | #7 |
|---|---|---|---|---|---|---|---|---|
| Brimonidine | 0.03% | 0.03% | 0.03% | 0.03% | 0.03% | 0.03% | 0.03% | |
| Poloxamer 407 | 5.5% | | | | | | | |
| HPBCD | | 5.5% | 5.5% | 5.5% | 5.5% | 5.5% | 5.5% | 5.5% |
| Aceclidine | 1.5% | 1.5% | 0.75% | 1.1% | 1.1% | 1.1% | 1.1% | 1.1% |
| Tropicamide | | | | 0.014% | 0.021% | 0.028% | 0.042% | 0.062% |
| NaCl | 0.25% | 0.25% | 0.25% | 0.25% | 0.25% | 0.25% | 0.25% | 0.25% |
| CMC | 0.75% | 0.75% | 0.75% | 0.75% | 0.75% | 0.75% | 0.75% | 0.75% |
| BAK | 0.1% | 0.1% | 0.1% | 0.1% | 0.1% | 0.1% | 0.1% | 0.1% |
| Redness (15 m) | 3+ | 1 | 0.5 | 0.5 | 0 | 0 | 0 | 0 |
| Redness (30 m) | 1.5 | 0.5 | 0.25 | 0.25 | 0 | 0 | 0 | 0 |
| Brow Ache (60 m) | 2+ | 2+ | 2 | 0.5 | 0.5 | 0.0 | 0.0 | 0.0 |
| Stinging (10 m) | 2 | 2 | 0.5 | 0 | 0 | 0 | 0 | 0 |
| BD-OD | 20.20 | 20.20 | 20.20 | 20.20 | 20.20 | 20.20 | 20.20 | 20.20 |
| BD-OS | 20.25 | 20.25 | 20.25 | 20.25 | 20.25 | 20.25 | 20.25 | 20.25 |
| BN-OD | 8 pt | 8 pt | 8 pt | 8 pt | 8 pt | 8 pt | 8 pt | 8 pt |
| BN-OS | 7 pt | 7 pt | 7 pt | 7 pt | 7 pt | 7 pt | 7 pt | 7 pt |
| BP-photopic | 3 mm | 3 mm | 3 mm | 3 mm | 3 mm | 3 mm | 3 mm | 3 mm |
| BP-mesopic | 5 mm | 5 mm | 5 mm | 5 mm | 5 mm | 5 mm | 5 mm | 5 mm |
| Miosis start (m) | 15 | 15 | 15 | 15 | 15 | 15 | 15 | 15 |

TABLE 2-continued

Effect of concentration of concentration of aceclidine and tropicamide.

|  | #1 | #2 | #3 | #4 | #5 (OD) | #5 (OS) | #6 | #7 |
|---|---|---|---|---|---|---|---|---|
| Miosis (OU) (1 hr) | 1.63 mm | 1.63 mm | 2.0-2.5 mm | 1.63 mm | 1.63 mm | 1.63 mm | 1.63 mm | 1.70 mm |
| Distance (OU) (20 m) | 20.20 | 20.20 | 20.20 | 20.20 | 20.20 | 20.20 | 20.20 | 20.20 |
| Distance (OD) (1 hr) | 20.15 + 2 | 20.15 + 2 | 20.20 | 20.15 + 2 | 20.15 + 2 | 20.15 + 2 | 20.15 + 2 | 20.15 + 2 |
| Distance (OS) (1 hr) | 20.15 + 2 | 20.15 + 2 | 20.20 | 20.15 + 2 | 20.15 + 2 | 20.15 + 2 | 20.15 + 2 | 20.15 + 2 |
| Disance (OU) (1 hr) | 20.10 − 3 | 20.10 − 3 | 20.15 | 20.10 − 3 | 20.10 − 3 | 20.10 − 3 | 20.10 − 3 | 20.10 − 3 |
| Near (OU) (20 m) | 4 pt | 4 pt | 4 pt | 4 pt | 4 pt | 4 pt | 4 pt | 4 pt |
| Time (hr) | 12.5 | 12.5 | 6.5 | 11 | 10 | 10 |  |  |

Abbreviations: (C) indicates corrected vision, (m) indicates minutes, (hr) indicates hour, mm indicates millimeters, BD indicates baseline distance vision; BN indicates baseline near vision, BP indicates baseline pupil size, OD indicates right eye; OS indicates left eye and OU indicates both eyes.
All percentages are w/v. "pt" reflects size of print materials, 4 being equivalent to 20/20 vision and 3 to 20/15 vision.
"Time" refers to duration of the effect.

As seen in Table 2 aceclidine at a concentration of at least 1.1% w/v was able to reduce the size of the pupil to 1.63 mm 1 hour after installation resulting in corrected near and distance vision for at least 10 hours. Lowering of the concentration of aceclidine to 0.75% w/v (formula #3) reduced the miotic effect to 2.0-2.5 mm after 1 hour and vision correction lasted only 6.5 hours. The addition of 0.03% w/v brimonidine reduced redness of the eye (4 out of 4 without brimonidine, not shown) to 1.5 out of 4 within 30 minutes after instillation which was maintained for the entire time vision was corrected. Switching the nonionic surfactant to HPβCD (formulas #2-6) further reduced the redness of the eye. Lowering of the concentration of aceclidine to 0.75% w/v (formula #3) further reduced eye redness but as mention above also reduced the vision correction duration of the formula.

A brow ache and stinging in the eye were noticeable in formulas #1-3 with a 2 out of 4 level of pain which was also associated with feelings of slight nausea, upset stomach and fatigue. Surprisingly, the addition of a cycloplegic agent, tropicamide, reduced brow ache and stinging to 0.5 out of 4 and 0 out of 4 respectively with brow ache dissipating after 60 minutes (formula #4). Further, the raising of the concentration of aceclidine to 1.1% w/v restored the longer duration of corrected vision seen in formulas #1-2 without increasing eye redness. However, upon re-instillation of formula #4 at the end of the 10 hours noticeable brow ache occurred. Instillation of formula #5 (OD) and (OS), with increased tropicamide concentrations, following formula #4 relieved the brow ache experienced with re-installation of formula #4. Upon a $3^{rd}$ instillation, at the end of the effective duration of formula #5, re-instillation of formula #5 again led to considerable brow ache. Once again, in formula #6, raising the concentration of tropicamide was able to overcome the brow ache. Additionally and unexpectedly, tropicamide, despite being a cycloplegic agent, had no effect on pupil miosis or vision correction. Surprisingly, the addition of tropicamide resulted in a prolonged duration of optimal pupil size constriction.

To determine the effect of brimonidine on pupil miosis, formula #7, was administered. Administration of formula #7 resulted in only a slight decrease in pupil miosis to 1.70 mm with identical distance and near vision improvement to that of formula #5. A 2-3+ conjunctival injection was noted.

All baseline vision data was based on vision corrected with distance contact lenses. Near vision was noted by subject as outstanding from 8 inches to the horizon at 1.5 hours after installation. A Marco Autorefractor with infrared camera and superimposed pupil calibration scale was used for all pupil size measurements. Once an image was selected it remained on screen allowing accurate calibration.

Example 3

TABLE 3

Effect of concentration of aceclidine, brimonidine, guanfacine, fadolmidine, tropicamide and additives.

|  | AB2T | AB4T | AB6T | AB11T | AB12T | PROPH13 |
|---|---|---|---|---|---|---|
| Aceclidine | 1.55 | 1.55 | 1.55 | 1.55 | 1.85 | 1.55 |
| Brimonidine | 0.037 | 0.037 | 0.037 | 0.037 |  |  |
| Fadolmidine |  |  |  |  |  | 0.037 |
| Guanfacine |  |  |  |  | 0.037 |  |
| HPBCD | 5.5 | 5.5 | 5.5 | 5.5 | 5.5 | 5 |
| Tropic amide | 0.043 | 0.043 | 0.043 | 0.043 | 0.042 | 0.043 |
| CMC* | 0.075 | 0.075 | 0.075 | 0.075 | 0.075 | 0.075 |
| NaCl | 0.025 | 0.025 | 0.025 | 0.025 | 0.025 | 0.025 |
| BAK | 0.01 | 0.01 | 0.01 | 0.01 | 0.01 | 0.01 |
| Glycerin | 0.1 |  | 0.1 |  |  | 0.1 |
| Poloxamer 188 | 0.1 | 0.05 |  |  |  |  |
| Polyoxyl 40 stearate |  | 0.05 |  |  |  |  |
| pH | 6.5 | 7.5 | 7.5 | 7.5 | 7.0 | 7.5 |
| nasal congestion | 0 | 0 | 0 | 0 | 0 | 0 |
| stinging initial | 0.75 | 0 | 1.5 | 3.5 | 0 | 1.5 |
| stinging, 3 min | 0.5 | 0 | 0 | wash out | 0 | 0 |

TABLE 3-continued

Effect of concentration of aceclidine, brimonidine, guanfacine, fadolmidine, tropicamide and additives.

|  | AB2T | AB4T | AB6T | AB11T | AB12T | PROPH13 |
|---|---|---|---|---|---|---|
| redness initial | 0 | 0 | 1 | D/C | 1 | 1 |
| redness 15 min | 0 | 0 | 0 | D/C | 0 | 0 |
| whitening | 0 | 0 | 0 | D/C | 1.5 | 1.5 |
| pain | 0 | 0 | 0 | D/C | 0 | 0 |
| vision near | 20.30 | 20.15 | 20.15 | D/C | 20.15 | 20.15 |
| vision distance | 20.20 | 20.20 | 20.20 | D/C | 20.20 | 20.20 |
| onset (min) | 20 | 12 | 16 | D/C | 12 | 16 |
| duration (hrs) | 5.5 | 7.5 | 7.5 | D/C | 7.5 | 7.5 |
| color | clear | yellow | yellow | yellow | yellow | yellow |
| OVERALL | 2.5 | 3.9 | 3.8 | 0 | 4 | 3.9 |

*1% = 2,500 cps
All percentages are w/v. Scores for nasal congestion, stinging initial, stinging, 3 min, redness initial, redness 15 min, whitening, pain and overall are out of 4.
"pt" reflects size of print materials, 4 being equivalent to 20/20 vision and 3 to 20/15 vision.
Baseline vision was 20.20 both eyes for distance; 20.70 right eye unaided for near; 20.80 left eye for near (best @ 16").
D/C stands for discontinued after eye washing due to intolerable stinging.

Aceclidine at a concentration of 1.55% w/v was able to reduce the size of the pupil to about 1.63 mm 30 minutes after instillation resulting in corrected near and distance vision to 20.20 or better for at least 6 hours, with noticeable affect lasting about 7.5 hours as seen in Table 3. Lowering of the concentration of aceclidine to 1.25% w/v (not shown) resulted in useful near vision improvement to about 20.25-20.30, but not as effective as at the higher dose range alkaline pH resulted in quicker onset, longer duration, and greater effect. The addition of 0.037% w/v brimonidine reduced redness of the eye (4 out of 4 without brimonidine, not shown) to baseline within 15 minutes after instillation which was maintained for the about the entire time vision was corrected. Adding glycerin 0.10% w/v noticeably reduced stinging. Adding instead poloxamer 188 0.05% w/v and polyoxyl 40 stearate 0.05% w/v however reduced initial stinging further but was more viscous. The combination of glycerin 0.1% w/v, poloxamer 188 0.1% w/v at a pH of 6.5 was noticeably reduced in onset, duration, comfort and effectiveness. AB11T did not include glycerin, poloxamer 188, or polyoxyl 40 stearate, which resulted in substantial stinging and discontinuation of the experiment with eye flush irrigation immediately after instillation. Substitution of guanfacine 0.037% w/v in AB12T for brimonidine resulted in minimal initial redness with prolonged redness reduction and some degree of whitening, and appeared to provide overall the best cosmesis though requiring slightly higher aceclidine concentration for optimal effect.

All baseline vision data was based on vision corrected with distance contact lenses. Near vision was noted by subject as outstanding from 8 to 10 inches to the horizon at 30 minutes after installation for AB4T and AB6T.

AB4T and AB6T were repeated both monocularly and binocularly. Substantial improvement in depth perception, near point acuity to 3 pt (20.15), and near point distance (8", 20.20) was noted when both eyes were treated vs. monocular treatment. Monocular treatment resulted in worsening of vision with both eyes open versus testing only the treated eye.

Example 4

TABLE 4

Effect of concentration of aceclidine, brimonidine, tropicamide, and additives.

|  | #8 | #9 | #10 | #11 | #12 | #13 | #14 |
|---|---|---|---|---|---|---|---|
| Aceclidine | 1.61% | 1.61% | 1.61% | 1.61% | 1.61% | 1.53% | 1.53% |
| Tropicamide | 0.042% | 0.042% | 0.042% | 0.042% | 0.042% | 0.044% | 0.044% |
| Brimonidine | 0.042% | 0.042% | 0.042% | 0.042% |  |  | 0.042% |
| CMC | 0.75% | 0.75% | 0.80% | 0.87% | 0.75% | 0.75% | 0.75% |
| NaCl | 0.25% | 0.25% | 0.50% | 0.50% | 0.25% | 0.50% | 0.50% |
| BAK | 0.01% | 0.01% | 0.01% | 0.01% | 0.01% | 0.01% | 0.01% |
| pH | 7.00 | 7.00 | 7.00 | 7.00 | 8.00 | 7.00 | 7.00 |
| phosphate buffer | 5 mM |  | 5 mM | 5 mM | 6 mM | 5 mM | 5 mM |
| borate buffer |  | 5 mM |  |  |  |  |  |
| Onset (min) | 15 | 15 | 15 | 15 | 15 | 15 | 15 |
| Duration (hrs) | 7 | 7 | 10-12 | 10-12 | 7 | 9 | 7 |
| Pupil range (mm) | 1.5-1.7 | 1.5-1.7 | 1.5-1.7 | 1.5-1.7 | 1.5-1.7 | 1.8-2.0 | 1.8-2.0 |
| Dimming 0-4 | 1.5 | 1.5 | 1.5 | 1.5 | 1.5 | 0.5 | 0.5 |
| Sting 0-4 | 1 | 1 | 1 | 1 | 1 | 1 | 1 |
| Ache 0-4 | 0.25 | 0.25 | 0.25 | 0.25 | 0.25 | 0.00 | 0.00 |
| Redness 0-4 | 0.5 | 0.5 | 0.5 | 0.5 | 1.5 | 1.0 | 0.5 |
| Other | watery | watery | sl thicker | sl residue | watery | watery | watery |
| Overall 0-5 | 3.5 | 3.5 | 4 | 4 | 2.5 | 4.5 | 4.75 |

TABLE 4-continued

Effect of concentration of aceclidine, brimonidine, tropicamide, and additives.

| | #15 | #16 | #17 | #18 | #19 | #20 | #21 |
|---|---|---|---|---|---|---|---|
| Aceclidine | 1.53% | 1.53% | 1.53% | 1.53% | 1.45% | 1.65% | 1.75% |
| Tropicamide | 0.044% | 0.044% | 0.044% | 0.044% | 0.042% | 0.044% | 0.035% |
| Brimonidine | 0.042% | 0.042% | | 0.042% | 0.042% | 0.042% | 0.042% |
| CMC | 0.80% | 0.80% | 0.80% | 0.80% | 0.75% | 0.75% | 0.75% |
| NaCl | 0.50% | 0.75% | 0.75% | 1.00% | 0.25% | 0.25% | 0.25% |
| BAK | 0.01% | 0.01% | 0.01% | 0.01% | 0.01% | 0.01% | 0.01% |
| pH | 7.00 | 7.00 | 8.00 | 7.00 | 7.00 | 7.00 | 8.00 |
| phosphate buffer | 5 mM | 5 mM | 5 mM | 5 mM | 5 mM | 5 mM | |
| borate buffer | | | | | | | 6 mM |
| Onset (min) | 15 | 15 | 15 | 15 | 15 | 15 | 15 |
| Duration (hrs) | 10-12 | 9 | 9 | 7 | 7 | 7 | 7 |
| Pupil range (mm) | 1.8-2.0 | 1.8-2.0 | 1.8-2.0 | 1.8-2.0 | 1.8-2.1 | 1.8-2.1 | 1.8-2.2 |
| Dimming 0-4 | 0.5 | 0.5 | 0.5 | 0.5 | 0.5 | 0.5 | 0.5 |
| Sting 0-4 | 1 | 1 | 1 | 1 | 1 | 1 | 1 |
| Ache 0-4 | 0.00 | 0.00 | 0.00 | 0.00 | 0.00 | 0.25 | 0.00 |
| Redness 0-4 | 0.5 | 0.5 | 1.0 | 0.5 | 0.5 | 0.5 | 0.5 |
| Other | sl thicker | sl thicker | sl thicker | thicker | watery | watery | watery |
| Overall 0-5 | 5 | 5 | 5 | 4 | 4 | 4 | 4 |

As seen in Table 4, formulas #8-9, an increase in brimonidine to 0.42% w/v resulted in redness reduction to 0.5, while 0.75% w/v CMC resulted in a watery consistency. Unexpectedly, increasing CMC from 0.75% w/v to a range of 0.80% w/v to 0.87% w/v and increasing NaCl from 0.25% w/v to 0.75% w/v in formulas #10-11 resulted in a thicker consistency and an increased residence time from 7 hours to 10-12 hours and decreased the amount of drug that drained into the nasolacrimal duct. This decreased drug delivery to the nasal passages results in less nasal congestion.

In formulas #13-18 a decrease in the amount of aceclidine from 1.61% to 1.53% w/v resulted in a pupil size range from 1.8-2.0 mm. Dimming as a result of the restriction of the pupil decreased linearly from 1.5 to 0.5 with the decreased amount of aceclidine. Specifically, the 1.8 to 2.0 mm pupil created 41% more light than the 1.5 to 1.7 mm pupil. Surprisingly, the 1.8 to 2.0 mm pupil had a near depth increase of 1.75 D. This is only a 0.25 D loss from the beneficial 2.00 D seen with the 1.5-1.7 mm range. Thus, the 1.80 to 2.0 mm range produces 41% more light while still allowing the full benefit of increased near vision in individuals under 60 years of age; whereas, individuals 60 years of age and over still experience total computer benefit and some increased near benefit.

The increase in tropicamide concentration from 0.042% w/v (formulas #8-#11) to 0.044% w/v (formulas #13-#18) resulted in a decrease in ache to negligible amounts. The amount of ache may also be correlated with the age of the individual. For those individuals under the age of 45, an increase of tropicamide concentration to a range from 0.046% to 0.060% w/v may be preferred.

Further, Table 4 shows an unexpected result seen in formulas #13 and #17 where the increase of NaCl from 0.25% w/v to a range of 0.50 to 0.75% w/v resulted in an acceptable redness score of only 1.0 even without the addition of the redness reducing agent brimonidine.

Formulas #15, #16 and #17 each result in an overall maximum rating of 5 by combining the benefits of: (1) reduced aceclidine concentrations to improve the amount of light produced without significantly affecting the near vision benefits seen in formulas #8-#12; (2) increased NaCl concentrations resulting in a further reduction in redness even in the absence of brimonidine; and (3) increased CMC concentrations resulting in longer residency time on the eye.

Formula #19 is an excellent alternative for the minority of individuals that are high responders to formulas #15-#17 and get noticeable dimming with 1.53% w/v aceclidine. Formula #20 is an excellent alternative for the minority of individuals that are low responders to formula #19. Lastly, Formula #21 is an excellent alternative for the minority of individuals that are low responders and get poor pupil response with Formula #20.

Example 5

TABLE 5

Comparison of Effects of Polyoxyl 40
Stearate, HPβCD and Poloxamer 407.

| | #22 | #23 | #24 |
|---|---|---|---|
| Aceclidine | 1.45% | 1.45% | 1.45% |
| Tropic amide | 0.044% | 0.044% | 0.044% |
| Brimonidine | 0.040% | 0.040% | 0.040% |
| Polyoxyl 40 Stearate | 5.5% | | |
| HPβCD | | 5.5% | |
| Poloxamer 407 | | | 5.5% |
| CMC | 0.80% | 0.80% | 0.80% |
| NaCl | 0.037% | 0.037% | 0.037% |
| EDTA | 0.015% | 0.015% | 0.015% |
| BAK | 0.007% | 0.007% | 0.007% |
| pH | 7.00 | 7.00 | 7.00 |
| phosphate buffer | 5 mM | 5 mM | 5 mM |
| Nasal Congestion | 0.00 | 0.50 | 1.50 |
| Stinging | 0.25 | 0.25 | 0.25 |
| Wetting | 4.00 | 4.00 | 4.00 |
| Redness | 0.25 | 0.50 | 0.50 |
| Visual Blur (<15 sec) | 0.50 | 0.50 | 1.50 |
| Duration | 6-8 hrs | 6-8 hrs | 6-8 hrs |
| Overall 0-4 | 4.00 | 4.00 | 4.00 |

Clinical Protocol 20 presbyopic patients with full distance correction were each given one of the above formulas (#22-#23). All patients received pre- and post-drop distance and near acuity measurement, Zeiss Visante® (Visante is a registered trademark of Carl Zeiss Meditec AG) optical adherence tomography, axial length and contrast acuity testing (i.e. Colenbrander-Michelson 10% Lum target) with the following results:

1) all patient achieved a miotic pupil of 1.5 to 2.20 mm;

2) no patient experienced ciliary ache, ciliary spasm, or induced accommodation;

3) all patients achieved 20/30+ visual acuity or better at 14" and were very satisfied with their high contrast near vision results and there was no significant complaint of burning or aching;
4) the duration of effect lasted 6-8 hrs in all cases;
5) binocular vision afforded all patients 1-1.5 additional lines of near acuity over monocular testing;
6) the last 10 patients were tested at 20" (i.e. computer distance, cell phone distance) and all achieved 20/25 or better near visual acuity;
7) moderately hyperopic (approx. +2.25 sphere) uncorrected presbyopes were very satisfied with distance visual acuity that improved to a 20/25 or better level at distance and near vision in the 20/30 range; and
8) uncorrected distance acuity was often improved for those patients who chose not to routinely correct a small refractive error.

As seen in Table 5, the use of polyoxyl 40 stearate provides the most comfortable aceclidine formulation with the least amount of visual blur and redness. To achieve similar results to that of formula #22, formula #23 requires 10-15% higher concentrations of the non-ionic surfactant and formula #24 requires 15-20% higher concentrations of the non-ionic surfactant. HPBCD induced a color change over time, possibly indicative of oxidation. Captisol® (sulfobutylether β-cyclodextrin) was substituted with similar findings.

Example 6

Modulation of Aceclidine Concentrations in a Preferred Embodiment

Preferred Embodiment:
Aceclidine 1.35%-1.55% w/v;
Polyoxyl 40 stearate 5.5% w/v;
NaCl 0.037% w/v;
CMC 0.80% w/v;
EDTA 0.015% w/v;
BAK 0.007% w/v;
Phosphate or Borate buffer 5 mM; and
pH 7.0.

For 1.35% w/v aceclidine—
1) Stinging on instillation 0.25/4.0 (lasting about 2-5 seconds);
2) Induced redness at 10 minutes: 1.0 to 1.5/4.0;
3) Induced redness at 30 minutes: 0.0 to 0.25/4.0;
4) Comfort: very high.
5) Wetting: very high, the eye maintaining sensation of improved wetting for most of a 24 hour period after a single instillation.
6) Depth of Focus distance: excellent.
7) Depth of Focus near: excellent.

In testing the above formulations on several subjects it was discovered that there is a slight range in clinical effect depending on the concentration of aceclidine, where 1.35%-1.55% w/v aceclidine is preferred, but for which 1.35% w/v and 1.45% w/v confer the desired benefits on most subjects. Further, it is discovered that the clinical effect of 1.35% w/v aceclidine can be improved when instilled as follows:
1) baseline effect: 1 drop to each eye.
2) enhanced effect: 2 drops to each eye.
3) greater effect: after 2) above repeat 1) above.
4) maximum effect: after 2) above repeat 2) above.

Example 7

Use of a Preferred Embodiment to Prolong Contact Lens Wear

Preferred Embodiment:
Aceclidine 1.45% w/v;
Polyoxyl 40 stearate 5.5% w/v;
NaCl 0.037% w/v;
CMC 0.80% w/v;
EDTA 0.015% w/v;
BAK 0.007% w/v;
Phosphate or Borate buffer 5 mM;
pH 7.0

As a baseline, the subject, who normally wore extended wear lenses (Air Optix®; Air Optix is a registered trademark of Novartis AG) for daily wear only, slept in these lenses overnight. On arising each morning the subject's vision was blurred and the contact lenses required removal and cleaning of film and deposits that had formed overnight. Average vision on arising at distance: 20.60; average vision at near on a Michelson contrast acuity chart: 20.80.

Then, for seven consecutive days the above formulation was instilled between 7 am and 10 am each day as a single dose. Subject wore the Air Optix® lenses throughout each day and slept in the lenses overnight. Upon arising each morning the subject's vision at distance: 20.20+; vision at near 20.40 unaided (consistent with subject's baseline presbyopia when the subject did not wear the lenses overnight and instead inserted the lenses upon arising).

Example 8

Table 6. Comparison of Effects of Polyoxyl 40 Stearate and Captisol® (sulfobutylether β-cyclodextrin).

TABLE 6

Comparison of Effects of Polyoxyl 40 Stearate and Captisol ® (sulfobutylether β-cyclodextrin).

|  | #25 | #26 | #27 | #28 | #29 | #30 | #31 | #32 | #33 |
|---|---|---|---|---|---|---|---|---|---|
| Aceclidine | 1.35% | 1.35% | 1.35% | 1.35% | 1.35% | 1.35% | 1.35% | 1.35% | 1.35% |
| Tropicamide | 0.044% | 0.044% | 0.044% | 0.044% | 0.044% | 0.044% | 0.044% | 0.044% | 0.044% |
| Polyoxyl 40 stearate | 5.5% | 5.5% | 5.5% | 5.5% | 5.5% | 5.5% | 5.5% |  |  |
| Captisol ® |  |  |  |  |  |  |  | 5.5% | 5.5% |
| Cocamidopropyl betaine |  |  |  |  |  |  | 0.10% |  |  |
| EDTA |  |  | 0.015% | 0.015% | 0.005% | 0.005% | 0.005% | 0.005% | 0.015% |
| CMC 1% = 2,500 cps | 0.80% | 0.80% | 0.80% | 0.80% | 0.80% | 0.80% | 0.80% | 0.80% | 0.80% |
| NaCl | 0.037% | 0.037% | 0.037% | 0.037% | 0.037% | 0.037% | 0.037% | 0.037% | 0.037% |
| Mannitol |  |  |  |  |  |  |  | 4% | 4% |
| BAK | 0.007% | 0.007% | 0.007% | 0.007% | 0.007% | 0.007% | 0.007% | 0.007% | 0.007% |

TABLE 6-continued

Comparison of Effects of Polyoxyl 40 Stearate and Captisol ® (sulfobutylether β-cyclodextrin).

|  | #25 | #26 | #27 | #28 | #29 | #30 | #31 | #32 | #33 |
|---|---|---|---|---|---|---|---|---|---|
| Borate buffer (mM) | 4 |  | 4 |  | 4 | 4 | 4 | 4 | 4 |
| Phosphate buffer (mM) |  | 4 |  | 4 |  |  |  |  |  |
| pH | 7 | 7 | 7 | 7 | 7 | 7 | 7 | 7 | 7 |
| Redness, 10 min | 1.25 | 1.25 | 2 | 2 | 1.75 | 1.75 | 0 | 0 | 0 |
| Redness, 30 min | 0 | 0 | 1.5 | 1.5 | 1.25 | 1.25 | 0 | 0 | 0 |
| Pupil, 30 min (mm) | <2 | <2 | <2 | <2 | <2 | <2 | <2 | <2 | <3 |
| Blur on instill (sec) | 10 | 10 | 10 | 10 | 10 | 10 | 10 | 10 | 10 |
| Ache | 0 | 0 | 0 | 0 | 0 | 0 | 1 | 0 | 0 |
| Rating | 4.00 | 4.00 | 2.00 | 2.00 | 2.50 | 2.50 | 1.00 | 5.00 | TBD |

As seen in Table 6, when using polyoxyl 40 stearate as the surfactant the exclusion of EDTA results in reduced redness and best overall rating among polyoxyl 40 stearate compositions (Formulas #25 and #26). The addition of cocamidopropyl betaine ("CAPB") further reduces redness however results in significant ache (Formula #31). Replacing polyoxyl 40 stearate with Captisol® (sulfobutylether β-cyclodextrin) and adding mannitol achieves similar results in redness reduction as the addition of CAPB to polyoxyl 40 stearate but without the attendant ache resulting in the highest overall rating among aceclidine compositions (Formula #32). After several weeks formulations with Captisol® (sulfobutylether β-cyclodextrin) had an orange hue, possibly indicative of oxidation.

Example 9

Use of a Preferred Embodiment

Composition Tested:
aceclidine at a concentration of about 0.5% w/v; and
poloxamer 188 at about 0.1% w/v;
poloxamer 407 at about 0.2% w/v;
polyoxyl stearate at about 5% w/v;
polyoxyl 35 castor oil at about 0.25% w/v;
carboxymethyl cellulose at a concentration of about 0.80% to about 0.85% w/v;
sodium chloride at a concentration of about 0.25% w/v;
optionally, BAK at a concentration of about 0.01% w/v;
citrate buffer at a concentration of about 0.02%;
with and without guanfacine at a concentration of about 0.03% w/v; and
wherein said composition has a pH of about 5.0 to about 8.0; and preferably, about 5.9 to about 6.2; and
wherein w/v denotes weight by volume The composition as described above was administered to a 61 year old subject and was reinstalled after 1 hour. It resulted in pupils of 1.6 mm ou, 20.20+ reading vision, and 20.20+ distance vision No ciliary spasm or loss of distance vision resulted. Transient redness of about 2+/out of 4 was noted for about 20 minutes without guanfacine, whereas transient redness of about 0.5+/out of 4 lasting less than 5 minutes was noted with guanfacine; otherwise the clinical results were identical. The presence or absence of BAK had no clinical effect, and was used to provide an optional preservative.

What is claimed is:

1. An ophthalmological composition for the treatment of presbyopia comprising aceclidine at a concentration from about 0.25% to about 2.0% w/v and a cycloplegic agent at a concentration from about 0.025% to about 0.1% w/v, wherein w/v denotes weight by volume.

2. The ophthalmological composition according to claim 1, wherein the cycloplegic agent is tropicamide.

3. The ophthalmological composition according to claim 1, further comprising brimonidine.

4. The ophthalmological composition according to claim 1 further comprising a surfactant selected from the group consisting of an anionic surfactant, a nonionic surfactant, and a combination thereof.

5. The ophthalmological composition according to claim 4 further comprising a viscosity enhancer.

6. The ophthalmological composition according to claim 5 wherein:
the viscosity enhancer is carboxymethyl cellulose or hydroxypropylmethyl cellulose;
the anionic surfactant is selected from the group consisting of a gamma cyclodextrin, sulfobutylether β-cyclodextrin, 2-hydroxypropyl cyclodextrin, sodium lauryl sulfate and sodium ester lauryl sulfate; and the nonionic surfactant is selected from the group consisting of polyoxyl stearate, a poloxamer, a polysorbate, sorbitan monolaurate, sorbitan monopalmitate, sorbitan monostearate, sorbitan monooleate, a polyoxyl alkyl, a polyoxyl stearate, a cyclodextrin and derivatives thereof.

7. The ophthalmological composition according to claim 2 wherein aceclidine is at a concentration from about 1.35% to about 1.55% w/v and tropicamide is at a concentration of about 0.042% w/v.

8. A method of treating presbyopia comprising administering to a subject in need thereof aceclidine at a concentration from about 0.25% to about 2.0% w/v and further comprising administering concurrently or sequentially an ophthalmological composition comprising a cycloplegic agent at a concentration from about 0.025% to about 0.1% w/v, wherein w/v denotes weight by volume.

9. The method of claim 8 wherein the cycloplegic agent is tropicamide at a concentration of 0.042% w/v and wherein the ophthalmological composition further comprises:
hydroxypropylmethyl cellulose;
sodium chloride at a concentration from about 0.05% to about 1.1% w/v;
glycerin at a concentration of about 0.2% w/v; and
citrate at a concentration of about 0.2% w/v or a phosphate buffer at a concentration from about 5 to about 10 millimoles, and
wherein w/v denotes weight by volume.

10. The method of claim 8 wherein the cycloplegic agent is tropicamide at a concentration of 0.042% w/v and wherein the ophthalmological composition further comprises:
hydroxypropylmethyl cellulose;
sodium chloride at a concentration from about 0.05% to about 1.1% w/v;

polyoxyl 40 stearate at a concentration of about 5.5% w/v; and citrate at a concentration of about 0.2% w/v or a phosphate buffer at a concentration from about 5 to about 10 millimoles, and wherein w/v denotes weight by volume.

11. The method of claim 8 wherein the aceclidine and the ophthalmological composition are administered from one device with at least two chambers and wherein the aceclidine resides in a first chamber and the ophthalmological composition resides in a second chamber and wherein the aceclidine first contacts the ophthalmological composition at the time of administration.

12. The method of claim 8 wherein the aceclidine resides in a first vial and the ophthalmological composition resides in a second vial and the aceclidine first contacts the ophthalmological composition at the time of administration.

13. The ophthalmological composition according to claim 7 further comprising a surfactant at a concentration of about 5.5% w/v.

14. The ophthalmological composition according to claim 13 wherein the surfactant is polyoxyl 40 stearate.

15. An ophthalmological composition for the treatment of presbyopia comprising aceclidine at a concentration from about 1.40 to about 1.45% w/v, tropicamide at a concentration of about 0.042% w/v, polyoxyl 40 stearate at a concentration of about 5.5% w/v, and hydroxypropylmethyl cellulose, wherein w/v denotes weight by volume.

* * * * *

UNITED STATES PATENT AND TRADEMARK OFFICE
CERTIFICATE OF CORRECTION

| | | |
|---|---|---|
| PATENT NO. | : 9,089,562 B2 | Page 1 of 1 |
| APPLICATION NO. | : 14/223639 | |
| DATED | : July 28, 2015 | |
| INVENTOR(S) | : Gerald Horn and Lee Nordan | |

It is certified that error appears in the above-identified patent and that said Letters Patent is hereby corrected as shown below:

Title Page, item (74), delete "Wood Phillips, Katz, Clark & Mortimer" and substitute therefor "Wood, Phillips, Katz, Clark & Mortimer"

In the Specification,

Column 31, Line 23, delete "1.63 min" and substitute therefor "1.63 mm"

Signed and Sealed this
Twenty-ninth Day of December, 2015

Michelle K. Lee
*Director of the United States Patent and Trademark Office*